US008345232B2

(12) United States Patent
Markwort et al.

(10) Patent No.: US 8,345,232 B2
(45) Date of Patent: Jan. 1, 2013

(54) OPTICAL INSPECTION SYSTEM AND METHOD

(75) Inventors: Lars Markwort, Haimhausen (DE);
Rajeshwar Chhibber, San Jose, CA
(US); Klaus Eckerl, Hutthurm (DE);
Norbert Harendt, Hutthurm (DE)

(73) Assignee: Nanda Technologies GmbH,
Unterschleissheim (DE)

( * ) Notice: Subject to any disclaimer, the term of this patent is extended or adjusted under 35 U.S.C. 154(b) by 14 days.

(21) Appl. No.: 12/916,315

(22) Filed: Oct. 29, 2010
(Under 37 CFR 1.47)

(65) Prior Publication Data

US 2011/0043796 A1   Feb. 24, 2011

Related U.S. Application Data

(63) Continuation of application No. 12/715,246, filed on Mar. 1, 2010, now Pat. No. 8,072,591, which is a continuation of application No. PCT/EP2009/002482, filed on Apr. 3, 2009.

(60) Provisional application No. 61/064,949, filed on Apr. 4, 2008.

(51) Int. Cl.
*G01N 21/00* (2006.01)
*G06K 9/00* (2006.01)

(52) U.S. Cl. ............ 356/237.2; 356/237.5; 382/145

(58) Field of Classification Search ............ None
See application file for complete search history.

(56) References Cited

U.S. PATENT DOCUMENTS

| | | | | |
|---|---|---|---|---|
| 2,313,460 A * | 3/1943 | Warmisham | ............ | 359/368 |
| 2,398,276 A * | 4/1946 | Altman | ............ | 359/422 |
| 2,441,036 A * | 5/1948 | Schade | ............ | 359/399 |
| 2,600,805 A * | 6/1952 | Reiss | ............ | 359/753 |
| 2,952,180 A * | 9/1960 | Estes | ............ | 396/380 |
| 3,176,583 A * | 4/1965 | Klein | ............ | 359/660 |
| 3,437,395 A * | 4/1969 | Rosenberger et al. | ........ | 359/363 |
| 4,009,945 A * | 3/1977 | Klein | ............ | 359/657 |
| 4,867,549 A * | 9/1989 | Sekine | ............ | 359/431 |
| 5,052,791 A * | 10/1991 | Kikuchi | ............ | 359/421 |
| 5,058,982 A | 10/1991 | Katzir | | |
| 5,175,652 A * | 12/1992 | Shimizu | ............ | 359/793 |
| 5,909,276 A | 6/1999 | Kinney et al. | | |
| 6,256,144 B1 * | 7/2001 | Kato | ............ | 359/432 |
| 6,491,836 B1 | 12/2002 | Kato et al. | | |
| 6,788,404 B2 | 9/2004 | Lange | | |

(Continued)

FOREIGN PATENT DOCUMENTS

WO   WO 2009/121628 A2   10/2009

(Continued)

OTHER PUBLICATIONS

Final Office Action for U.S. Appl. No. 12/715,246 mailed on May 12, 2011, 9 pages.

(Continued)

*Primary Examiner* — Gordon Stock, Jr.
(74) *Attorney, Agent, or Firm* — Silicon Valley Patent Group LLP

(57) ABSTRACT

An inspection system includes imaging optics for imaging an object plane into an image plane. The imaging optics include an objective lens having positive optical power, a first lens group having negative optical power, and a second lens group having positive optical power. The optical elements are arranged along a common unfolded optical axis with a pupil plane of the imaging optics located between the first lens group and the second lens group.

17 Claims, 12 Drawing Sheets

U.S. PATENT DOCUMENTS

| | | | |
|---|---|---|---|
| 6,853,446 | B1 | 2/2005 | Almogy et al. |
| 6,999,183 | B2 | 2/2006 | Nielsen et al. |
| 7,130,036 | B1 | 10/2006 | Kuhlmann et al. |
| 7,312,432 | B2 | 12/2007 | Liang |
| 7,345,825 | B2 | 3/2008 | Chuang et al. |
| 7,782,452 | B2 | 8/2010 | Mehanian et al. |
| 8,072,591 | B2 | 12/2011 | Markwort et al. |
| 8,102,521 | B2 | 1/2012 | Markwort et al. |
| 2004/0207836 | A1 | 10/2004 | Chhibber et al. |
| 2006/0219930 | A1 | 10/2006 | Lange |
| 2007/0013661 | A1 | 1/2007 | Theytaz et al. |
| 2007/0121106 | A1 | 5/2007 | Shibata et al. |
| 2009/0161096 | A1 | 6/2009 | Vaez-Iravani et al. |
| 2009/0219518 | A1 | 9/2009 | Baldwin et al. |
| 2010/0231902 | A1 | 9/2010 | Markwort et al. |
| 2011/0043798 | A1 | 2/2011 | Markwort et al. |
| 2012/0133760 | A1 | 5/2012 | Markwort et al. |

FOREIGN PATENT DOCUMENTS

| | | | |
|---|---|---|---|
| WO | WO 2009/121628 | A9 | 10/2009 |

OTHER PUBLICATIONS

Final Office Action for U.S. Appl. No. 12/916,336 mailed on Jun. 30, 2011, 6 pages.

International Preliminary Report on Patentability mailed on Oct. 5, 2010 for PCT Application No. PCT/EP2009/002482 filed on Apr. 3, 2009, 8 pages.

U.S. Appl. No. 12/715,246, filed on Mar. 1, 2010 by Markwort et al., 45 pages.

U.S. Appl. No. 12/916,336, filed on Oct. 29, 2010 by Markwort et al., 45 pages.

U.S. Appl. No. 13/277,986, filed on Oct. 20, 2011 by Markwort et al., 44 pages.

Preliminary Amendment mailed on Feb. 10, 2012 for U.S. Appl. No. 13/277,986, filed on Oct. 20, 2011 by Markwort et al., 7 pages.

Office Action mailed on May 15, 2012 for U.S. Appl. No. 13/277,986, filed on Oct. 20, 2011 by Markwort et al., 8 pages.

Office Action mailed on Feb. 22, 2011 for U.S. Appl. No. 12/916,336, filed on Oct. 29, 2010 by Markwort et al., 12 pages.

Examiner Interview Record mailed on Apr. 25, 2011 for U.S. Appl. No. 12/916,336, filed on Oct. 29, 2010 by Markwort et al., 3 pages.

Response to Office Action mailed on Apr. 29, 2011 for U.S. Appl. No. 12/916,336, filed on Oct. 29, 2010 by Markwort et al., 12 pages.

Final Office Action mailed on Jun. 30, 2011 for U.S. Appl. No. 12/916,336, filed on Oct. 29, 2010 by Markwort et al., 6 pages.

Response to Final Office Action mailed on Aug. 31, 2011 for U.S. Appl. No. 12/916,336, filed on Oct. 29, 2010 by Markwort et al., 6 pages.

Examiner Interview Summary Record and Notice of Allowance mailed on Sep. 22, 2011 for U.S. Appl. No. 12/916,336, filed on Oct. 29, 2010 by Markwort et al., 12 pages.

Preliminary Amendment mailed on May 17, 2010 for U.S. Appl. No. 12/715,246, filed on Mar. 1, 2010 by Markwort et al., 3 pages.

Office Action mailed on Oct. 7, 2010 for U.S. Appl. No. 12/715,246, filed on Mar. 1, 2010 by Markwort et al., 10 pages.

Response to Office Action mailed on Mar. 2, 2011 for U.S. Appl. No. 12/715,246, filed on Mar. 1, 2010 by Markwort et al., 14 pages.

Final Office Action mailed on May 12, 2011 for U.S. Appl. No. 12/715,246, filed on Mar. 1, 2010 by Markwort et al., 9 pages.

Response to Final Office Action mailed on Aug. 1, 2011 for U.S. Appl. No. 12/715,246, filed on Mar. 1, 2010 by Markwort et al., 5 pages.

Examiner Interview Summary Record and Notice of Allowance mailed on Aug. 25, 2011 for U.S. Appl. No. 12/715,246, filed on Mar. 1, 2010 by Markwort et al., 12 pages.

* cited by examiner

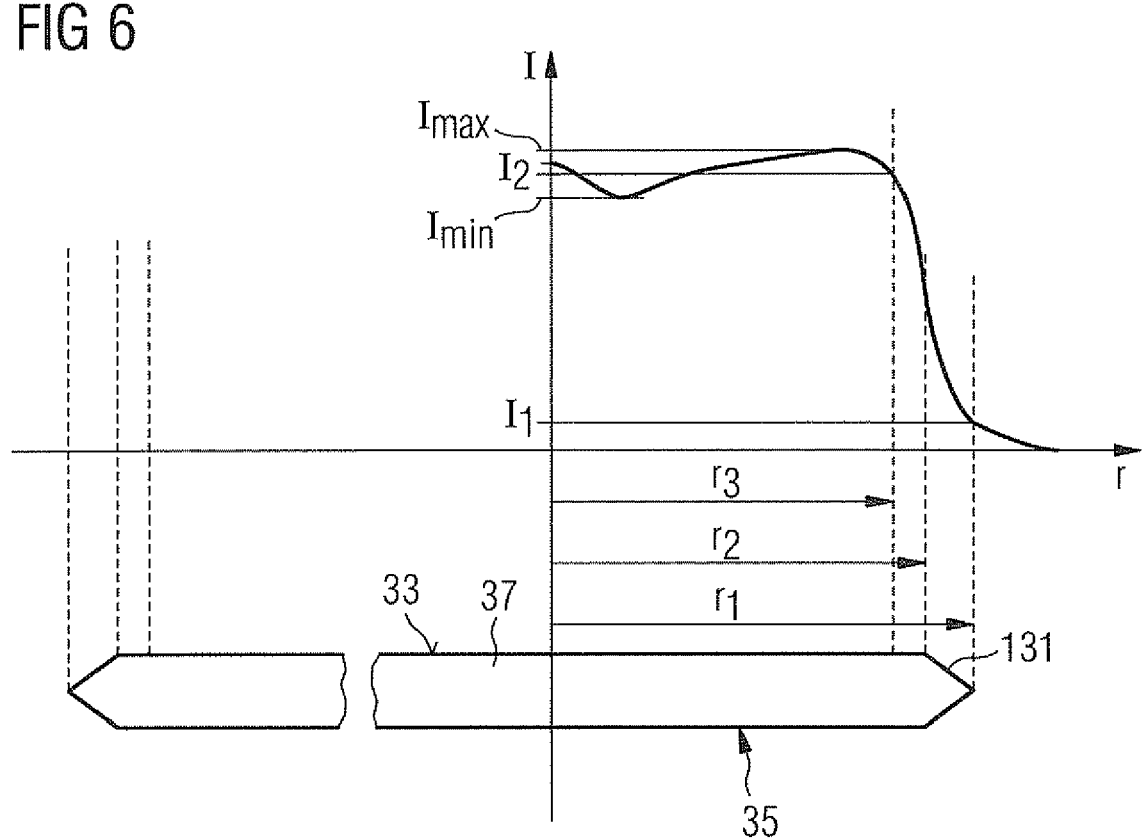

OPTICAL INSPECTION SYSTEM AND METHOD

CROSS-REFERENCES TO RELATED APPLICATIONS

This application is a continuation of U.S. application Ser. No. 12/715,246, filed Mar. 1, 2010; which claims priority to and is a continuation of International Patent Application No. PCT/EP2009/002482, filed Apr. 3, 2009, which claims the benefit of U.S. Provisional Patent Application No. 61/064,949, filed Apr. 4, 2008. The disclosures of PCT/EP2009/002482 and 61/064,949 are hereby incorporated by reference in their entirety for all purposes.

BACKGROUND OF THE INVENTION

The present invention relates to optical inspection systems and methods.

Objects of inspection can be generally any types of objects and, in particular, semiconductor wafers. In semiconductor wafer applications, the invention is directed to so-called macro-defect inspection.

SUMMARY OF THE INVENTION

Semiconductor circuits are manufactured by forming micropatterned structures on a flat semiconductor wafer substrate using lithographic methods. A wafer substrate may have a diameter of about 300 mm, wherein several hundred circuits are arranged in individual dies typically having diameters in the order of some millimeters to some ten millimeters, wherein the structures of the semiconductor circuits may have dimensions below 0.1 µm. It is desirable to detect defects in the manufactured patterns and deficiencies of a manufacturing process at early stages of the semiconductor manufacture. Several techniques are known for inspection of semiconductor substrates.

FIG. 1 is a schematic illustration of a micro-defect inspection system aiming to detect deficiencies in the smallest patterned structures having dimensions of 0.1 µm and below. FIG. 1 schematically indicates a wafer 1 having an array of rectangular dies 3 formed on its surface. The wafer 1 is mounted on a wafer stage 5 which is configured to translate and rotate the wafer relative to an objective lens 7 of a microscope 9. The microscope includes an image sensor 11, a light source 13 and a beam splitter 15. A portion of a measuring light beam 17 generated by the light source is reflected from the beam splitter 15, traverses the objective lens 7 and is focused by the objective lens to illuminate a small portion of the surface of the wafer 1. This illuminated portion of the wafer is further imaged onto the image sensor 11 such that a magnified microscopic image of the small portion of the surface of the wafer can be detected. Comparing the detected image with a desired image of this small portion allows to eventually detect a defect or deficiency of a manufactured structure on the wafer. By translation of the wafer relative to the optics, it is possible to detect images of other portions of the wafer surface. Micro-defect inspection methods, such as the one illustrated above with reference to FIG. 1, have the advantage of detecting defects and deficiencies in very small structures of the manufactured semiconductor, but they have the disadvantage of a low throughput, since it will take considerable time to obtain images of all portions of the wafer surface. Other known micro-defect inspection methods include laser scanning methods and electron microscopic methods.

FIG. 2 illustrates a macro-defect inspection system in which a larger portion including plural dies 3 on a surface of a wafer 1 or the whole wafer surface is imaged onto an image sensor 11. Since a size of available image sensors is typically smaller than a size of the imaged area on the wafer, an imaging optics, schematically indicated at 19, is typically a de-magnifying optics. A dark field light source 21 is provided to generate a dark field illumination beam 22 directed under an acute angle onto the wafer surface such that a main portion of the incident dark field illumination light beam is specularly reflected from the wafer surface to be trapped in a beam dump 23. Defects on the wafer surface, such as small particles or scratches will scatter incident dark field illumination light such that it is collected by the imaging optics 19 and detectable by the image sensor 11. Alternatively or in addition thereto, a bright field light source 25 can be provided to generate a bright field illumination light beam 26 incident onto the wafer surface such that a main portion of the bright field illumination light beam 26 reflected from the wafer surface is also collected by the imaging optics 19 and detected by the image sensor 11. Macro-defect inspection methods as illustrated above with reference to FIG. 2 have the advantage of high throughput since an image of a relatively large portion of the wafer surface can be obtained in a short time, but they have a disadvantage that small defects on the wafer are not detectable due to a limited resolution of available image sensors. Still, macro-defect inspection methods are capable of detecting a large number of possible defects and deficiencies occurring during semiconductor wafer manufacture.

Therefore, it is desirable to have optical macro-defect inspection systems and methods allowing for a high throughput and high imaging quality.

The present invention has been accomplished taking the above problems into consideration.

It is an object of the present invention to provide an optical inspection system and method allowing for high throughput and high imaging quality.

Embodiments of the present invention provide inspection systems and methods allowing for high throughput and high imaging quality.

Particular embodiments of the invention provide macro defect inspection systems and methods for optical inspection of patterned and unpatterned wafers.

Embodiments of the present invention provide an inspection system comprising optics and an image detector having a radiation sensitive substrate disposed in a region of an image plane of the optics, wherein the optics and image detector are configured such that a relatively large object field are imaged onto the radiation sensitive substrate, wherein a diameter of an object field imaged onto the radiation sensitive substrate is greater than 0.6 times the wafer diameter, wherein the wafer diameter can be 300 mm or more, such as 400 mm, for example. In other embodiments herein, the diameter of the object field can be greater than 0.7 or 0.8 times the wafer diameter, or correspond to a full wafer diameter.

According to other embodiments, the diameter of the object field can be greater than 200 mm, greater than 250 mm or greater than 300 mm while a total extension of an imaging beam path from the object plane to the image plane is less than 1500 mm, less than 1300 mm, less than 1100 mm or less than 900 mm. According to other embodiments, the total extension of the imaging beam path from the object plane to the image plane divided by the object field diameter, can be less than 6.0, in particular less than 5.0, and according to other exemplary embodiments, less than 4.0.

With such configuration it is possible to obtain an image of a large portion of the wafer surface or of the complete wafer surface using optics which have a comparatively short longitudinal extension along its unfolded optical axis. It is then possible to incorporate the necessary optics of the inspection system in a volume which is relatively small such that the system can be easily integrated in an existing tool chain of a semiconductor manufacturing facility.

According to embodiments of the invention, the imaging from the wafer to the detector is a de-magnifying or reducing imaging having a magnification of less than 1.0.

In particular embodiments, the magnification is less than 0.25 or less than 0.20.

According to some embodiments of the inspection system, the system comprises a bright field light source, and the optics comprises an objective lens and a beam splitter arranged to provide both an imaging beam path and a bright field illumination beam path. For this purpose, the components are arranged such that the object plane, the objective lens, the beam splitter and the radiation sensitive substrate are arranged in this order in the imaging beam path, and the beam splitter, the objective lens and the object plane are arranged in this order in the bright field illumination beam path.

With such arrangement it is possible to integrate the bright field illumination optics or the imaging optics without significantly increasing the total volume occupied by the system and compared to conventional arrangements of integrating large field imaging with bright field illumination (such as shown in FIG. 2). As used in the present application, the term "bright field illumination" designates a configuration in which an illuminating light ray which is incident on the flat substrate surface and scattered at the surface by an angle of less than 20° relative to its specular reflection direction can be collected by the imaging optics. On the other hand, the term "dark field illumination" as used in the present application designates a configuration where incident illumination light rays must be scattered by more than 30° relative to their specular reflection directions to be collected by the imaging optics.

According to embodiments of the invention, the inspection system comprises imaging optics for imaging the object field onto the radiation sensitive substrate of the image detector, and wherein the imaging optics consists of an objective lens having positive optical power, a first lens group having negative optical power and a second lens group having positive optical power, wherein the objective lens, the first lens group and the second lens group are arranged in this order along a common unfolded optical axis, and wherein a pupil plane of the imaging beam path is located between the first and second lens groups. According to an embodiment, the length measured along the unfolded optical axis, from a lens surface of the objective lens closest to the image plane, to a lens surface of the first lens group located closest to the object plane, is greater than a diameter of an object field imaged into the image plane.

According to an embodiment herein, the objective lens is a single non-cemented lens element having two lens surfaces, wherein that surface having the greater surface curvature fulfils the following relation: the free diameter of the lens divided by the radius of curvature of the surface having the greater curvature is greater than 0.5, greater than 0.7 or greater than 0.9. Such objective lens has a high optical power. Conventional imaging applications requiring a high imaging quality use objective lenses comprising two or more lens elements and/or cemented lens elements to reduce chromatic and spherical errors generated by the high optical power of the lens. According to this embodiment of the invention, the high diameter and high power non-cemented lens element generate a relatively high chromatic error and a relatively high spherical error which are compensated for by the first lens group. With such configuration, a high imaging quality can be maintained while allowing for a simple configuration of the objective lens. In particular, in applications where the objective field diameter is large, such as 300 mm and more, and where the diameter of the objective lens has to be somewhat greater than the diameter of the object field, a cemented lens element of that size can be very expensive. Due to the compensation of the chromatic error and/or spherical error introduced by an objective lens, a light weight and inexpensive single lens element can be used as the objective lens.

According to an exemplary embodiment herein, the single non-cemented lens element has a spherical lens surfaces and, according to a particular embodiment, one spherical surface and one flat surface (having an infinite radius of curvature). According to a particular embodiment herein, the curved surface of the single lens element is oriented towards the object while the flat surface is oriented towards the image detector.

According to an embodiment of the invention, the inspection system comprises an object support for mounting an object having a predetermined periphery shape, an image detector and optics for imaging the object including its periphery onto a radiation sensitive substrate of the image detector. The inspection system further comprises a bright field light source for supplying a bright field illumination light beam incident on the object such that the periphery of the object receives bright field illumination light. The optics comprises an objective lens, first, second and third lens groups and a field aperture. The following elements are arranged in the imaging beam path in that order: the object plane, the objective lens, the second lens group and the radiation sensitive substrate of the image detector. An object field which is imaged onto the radiation sensitive substrate has a diameter of more than 300 mm. Further, the following elements are arranged in the bright field illumination beam path in that order: the bright field light source, the third lens group, the first field aperture, the second lens group, the objective lens and the object plane. The elements of the bright field illumination beam path are arranged such that the periphery of the object receives a low intensity of the bright field illumination light while an interior of the object surface receives a high intensity of the bright field illumination light. With such arrangement it is possible that also the periphery of the object is apparent in the detected image such that a position of the object within the image can be precisely determined. It is then possible to establish a precise correspondence or transformation between locations within the image and corresponding locations in a coordinate system attached to the object. However, since object peripheries typically generate a very high reflected radiation intensity, it is desirable to prevent bright field illumination light from being incident onto the periphery of the object to avoid excessive light intensities being incident onto the detector and to avoid high stray light intensities which can deteriorate an image quality of interior portions of the object surface. According to this embodiment of the invention, the periphery receives a substantially reduced light intensity sufficient to determine the periphery of the object within the detected image, and the light intensity rises to its full intensity within a carefully selected distance from the periphery.

According to an exemplary embodiment of the present invention, the illumination light intensity rises from a value between 0.001 and 0.010 times a maximum illumination intensity at a periphery of the illuminated field to a value of more than 0.900 times a maximum illumination intensity within a length of 3 mm to 6 mm.

According to an embodiment of the present invention, the inspection system provides an imaging beam path and a dark field illumination beam path, wherein both the imaging beam path and the dark field illumination beam path are designed such that an angular variation of rays of the respective beam path across the object plane is low. This means that, at a given location on the object plane, the incident dark field illumination light appears to originate from a relatively narrow cone, and that such cone has a substantially same orientation for all locations within the object plane. Similarly, among all rays emanating from the object plane at a given location, only a relatively narrow cone is used for imaging of the object plane onto the detector, and orientations of such cones for all possible locations on the object plane are substantially the same.

According to an exemplary embodiment herein, a variation of an orientations of chief rays of the illumination beam path across the object field is less than 5°. As used herein, chief rays are those rays of a beam path which traverse a pupil plane of the respective optics on an optical axis thereof.

According to a further exemplary embodiment, a variation of orientations of chief rays of the imaging beam path is less than 5°.

According to a further exemplary embodiment, a numerical aperture of the imaging beam path on a side of the object plane is less than 0.1, less than 0.08, less than 0.06, less than 0.04, or less than 0.02. As used herein, the term "numerical aperture" designates the sine of the vertex angle of the largest cone of light rays incident on or emanating from the considered plane and traversing the respective optics.

According to a further exemplary embodiment, a numerical aperture of the illumination beam path on the side of the object plane is less than 0.1, less than 0.08, less than 0.06, less than 0.04, or less than 0.02.

The inspection system having telecentric dark field illumination and telecentric imaging beam paths is advantageously suitable for inspecting large object surfaces carrying periodic structures. Such periodic structures may form a Bragg grating for the incident dark field illumination light such that the incident light is diffracted into a direction accepted by the imaging optics. Regions of the object fulfill a Bragg condition relative to the illumination beam path and the imaging beam path will then appear as very broad regions outshining features of the inspected object. This means that features of the inspected object located at those positions where the Bragg condition is fulfilled are not detectable. Due to the telecentric illumination and imaging beam paths substantially the same angular regulations between incident light and light used for imaging are fulfilled across the whole surface of the inspected object. Therefore, a Bragg condition will be fulfilled or not fulfilled for substantially the whole inspected surface. It is then possible to change a lattice period of the periodic structures as seen by the dark field illumination light by rotating the object about an optical axis of the imaging beam path such that a Bragg condition can be avoided for the whole inspected surface. A dark field image of the inspected object can be detected without deterioration by Bragg diffraction, accordingly.

According to exemplary embodiments of the invention, the dark field illumination beam path includes a beam dump for absorbing dark field illumination light reflected from the object surface.

According to a particular embodiment herein, the beam dump comprises first and second light absorbing portions wherein the first light absorbing portion is arranged to receive a portion of the illumination beam reflected from the inspected object on a surface thereof. The second light absorbing portion of the beam dump is then arranged such that it receives, on a surface thereof, a portion of the illumination light reflected from the surface of the first light absorbing portion. The first light absorbing portion is made of a transparent light absorbing material such as dark glass. According to exemplary embodiments of the invention, the absorbing material is configured such that an intensity $I_t$ of light transmitted through a plate having a thickness of 1 mm when an intensity $I_0$ of light is incident on the plate fulfils the following relation: $1\times10^{-7} \leq I_t/I_0 \leq 0.8$ within a wavelength range from 200 mm to 800 mm.

According to a further exemplary embodiment, also the second light absorbing portion is made of a light absorbing material. According to further exemplary embodiments, the light receiving surface of the first light absorbing portion and/or the second light absorbing portion carries an anti-reflective coating.

With such beam dump it is possible to effectively absorb dark field illumination light reflected from the object and prevent stray light within a compartment of the inspection system. A main portion of the light incident on the first light absorbing portion is absorbed within the bulk of the absorbing material, and only a small portion of this light is reflected from the surface of the first light absorbing portion and then absorbed by the second light absorbing portion.

According to further embodiments of the invention, the optics provides an imaging beam path, a bright field illumination beam path and a dark field illumination beam path, wherein one or more folding mirror surfaces are disposed in each of the beam paths for achieving a small total volume which the complete system occupies.

According to an exemplary embodiment, the imaging beam path includes the object plane, the objective lens, a first folding mirror, a beam splitter and the radiation sensitive surface of the detector; the bright field illumination beam path includes the bright field light source, the beam splitter, the first folding mirror, the objective lens and the object plane; and the dark field illumination beam path includes the dark field light source, a projection lens, a second folding mirror, the object plane and the beam dump. According to an exemplary embodiment herein, when seen projected onto a plane parallel to the object plane, an angle between an optical axis of the imaging beam path in a portion between the first mirror and the beam splitter and an optical axis of the dark field illumination beam path in a portion between the second mirror and the beam dump is less than 70°.

According to an exemplary embodiment herein, the beam splitter is located closer to the projection lens than to the beam dump. According to a further exemplary embodiment herein, the dark field light source is located closer to the beam dump than to the beam splitter.

According to a further exemplary embodiment, the system comprises an object supply apparatus for loading objects into the system. Such supply apparatus is configured to translate the objects in a loading direction, wherein, when seen projected onto the plane parallel to the object plane, an angle between the loading direction and the portion of the dark field illumination beam path between the third mirror and the beam dump is smaller than an angle between the loading direction and the portion of the imaging beam path between the first folding mirror and the beam splitter.

According to further embodiments of the invention, the inspection system maintains a high imaging quality also in presence of vibrations which may be induced by components of the inspection system itself or by vibration sources outside of the inspection system.

According to an embodiment herein, the inspection system comprises a common base structure supporting all components of the system, wherein the optics provides an imaging beam path including the object plane, the objective lens, the first folding mirror, the beam splitter and the radiation sensitive surface of the detector, and a bright field illumination beam path comprising the bright field light source, the beam splitter, the first folding mirror, the objective lens and the object plane, and wherein at least one of a frame of the objective lens and a frame of the first folding mirror is mounted to and carried by a first optics carrier which is mounted to and carried by the base.

According to an exemplary embodiment herein, the image detector is mounted to and carried by the frame of the objective lens and/or the frame of the first mirror. This may have an advantage of forming rigid chain of supporting structures for the components of the imaging beam path from the objective lens and the first folding mirror via the beam splitter to the detector.

According to a further exemplary embodiment, the optics provides a dark field illumination beam path including a dark field light source which is mounted to and carried by a second optics carrier which is mounted to and carried by the base. The first and second carriers are commonly mounted on the base but are separate mechanical structures which are not otherwise connected to each other. Such arrangement may have an advantage in that vibrations originating from a cooling system of the dark field light source will not directly induce vibrations of the objective lens and/or the first folding mirror.

According to a further exemplary embodiment, an object support arranged for mounting the object to be inspected is mounted to and carried by the common base without further mechanical connection to the first or second carriers.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

FIG. 6 is a schematic illustration of a bright field light intensity achieved with the beam path shown in FIG. 5;

DETAILED DESCRIPTION OF THE INVENTION

Figure 1:
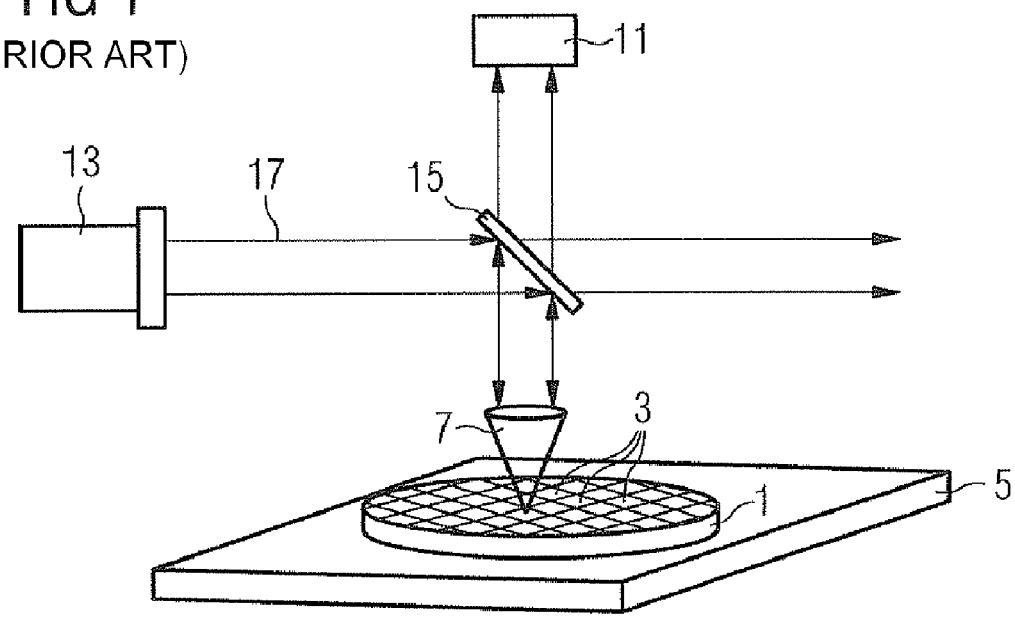
FIG. 1 is a schematic illustration of a conventional micro-defect inspection system.
Figure 2:
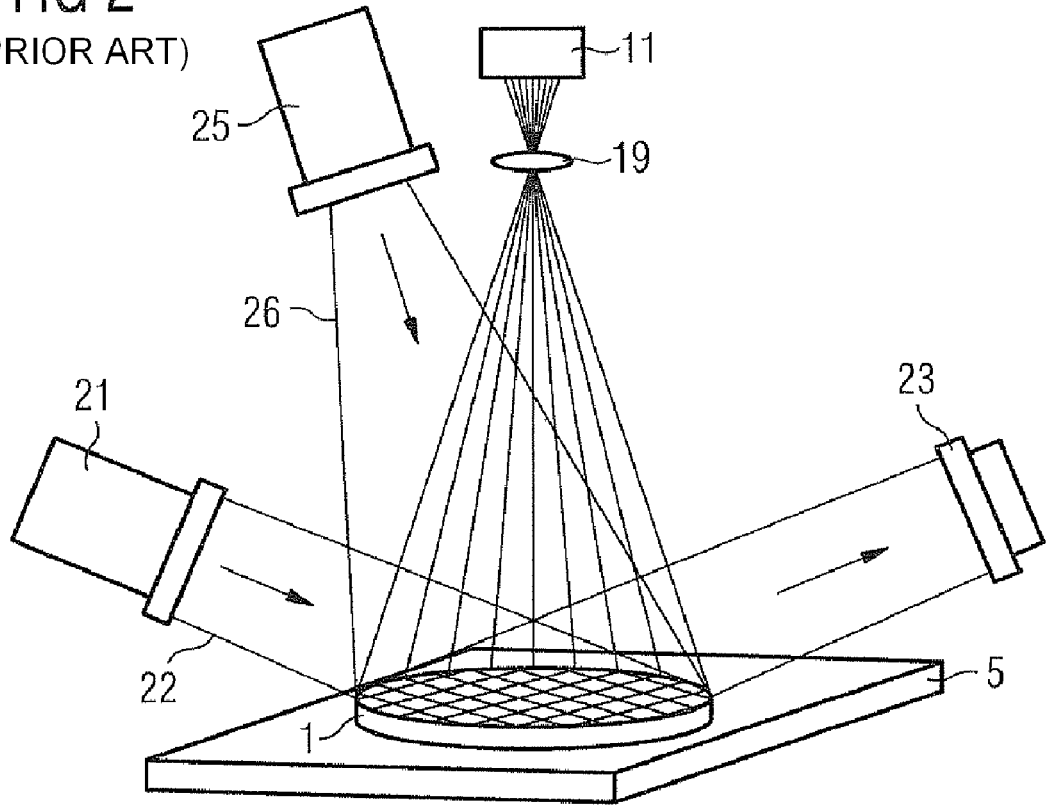
FIG. 2 is a schematic illustration of a conventional macro-defect inspection system.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

Figure 3:
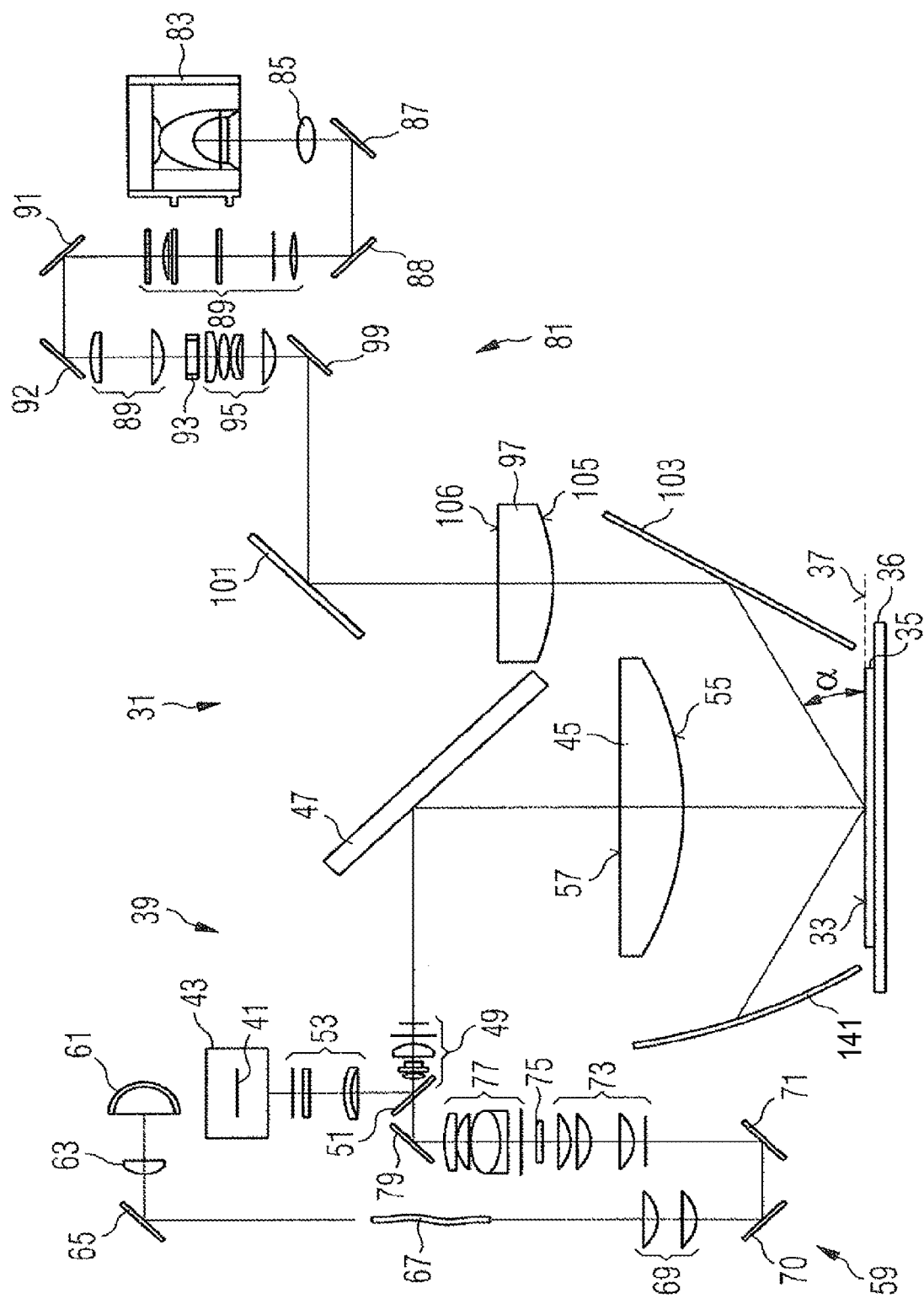
FIG. 3 is a schematic illustration of a macro-defect inspection system according to an embodiment of the invention.

FIG. 3 is a schematic illustration of a macro-defect inspection system according to an embodiment of the present invention.

The system 31 is designed to obtain images of surfaces 33 of semiconductor wafers 35. In this embodiment, the wafers 35 are wafers currently used in semiconductor manufacturing having a diameter of about 300 mm. However, the present invention is not limited to such wafer diameters and can be applied to other wafer diameters, such as 400 mm or more which may be used in the future. Moreover, the present invention is generally applicable to inspection of other objects, which may be different from semiconductor wafers and include objects such as data carriers, biological samples, chemical processing systems and so on.

The wafer 35 is mounted on an object support 36 such that its surface 33 is disposed in an object plane 37 of an imaging beam path 39 of the system 31. The imaging beam path 39 is configured and arranged to image the full surface 33 of the wafer 35 onto a radiation sensitive substrate 41 of an image detector 43. For this purpose, the imaging beam path 39 comprises an objective lens 45, a folding mirror 47, a first lens group generally indicated at 49, a beam splitter 51, a second lens group generally indicated at 53 and the radiation sensitive surface 41 of the image detector 43. The imaging beam path 39 is telecentric on the side of the object plane 37 and it is also telecentric on the side of its image plane which coincides with the radiation sensitive surface 41. Due to the telecentric property on the side of the object plane 37, a diameter of the objective lens 45 is greater than the diameter of the wafer surface 33. However, in embodiments where the telecentric property on the side of the object plane 37 is not required, it is possible to use objective lenses of a reduced diameter. Further, in the embodiment schematically shown in FIG. 3, the objective lens 45 is represented as a single non-cemented lens element having a convex surface 55 oriented towards the object plane 37 and a substantially flat surface 57 oriented towards the image plane 41. It is to be noted that other embodiments of the invention may comprise other types of objective lenses comprising one single lens element having two curved surfaces and which may comprise cemented lens elements, and other objective lenses may also comprise two or more lens elements.

While the objective lens 45 has positive optical power, the lens group 49 has negative optical power, the lens group 53 has positive optical power, and the beam splitter 51 is disposed in a space between the first and second lens groups 49, 53.

The beam splitter 51 has a function of separating the imaging beam path 39 from a bright field illumination beam path 59. The bright field illumination beam path 59 comprises a bright field light source 61, a collimating lens 63 which may comprise one or more individual lens elements and a mirror 65. The light source 61 is in this exemplary embodiment a xenon-arc lamp having a power of 35 W and emitting light in a broad spectral range. The lamp 61 has a window having a function of an IR filter such that light having wavelength above 800 nm is substantially not transmitted towards the wafer 35. The light reflected from the mirror 65 is coupled into an optical fiber 67 which is flexible and allows mounting of the bright field illumination light source 61 such that vibrations induced by a cooling system of the light source 61 are decoupled from a remaining portion of the bright field illumination system and the imaging system.

The bright field illumination light emerging from the optical fiber 67 is collimated by a lens group 69 and reflected from two mirrors 70, 71 before it enters an optical element group 73. The group 73 has a function of shaping the bright field illumination light beam such that an aperture 75 is homogenously illuminated. For this purpose, the lens group 73 comprises lenses and one or more optical integrators which may comprise fly eye lenses and/or glass rods. The aperture 75 is a field aperture and defines the portion of the object plane 37 which is illuminated with bright field illumination light. To achieve this, the bright field illumination optics is configured such that the field aperture 75 is imaged onto the wafer surface 33 which coincides with the object plane 37 of the imaging beam path. The bright field illumination light having traversed the field aperture 75 is manipulated by a lens group 77, reflected from a mirror 79, traverses the beam splitter 51 and the lens group 49, is reflected from the mirror 47 and traverses the objective lens 45 to be incident on the object plane 37.

In the embodiment shown in FIG. 3, the beam splitter 51 is traversed by the bright field illumination beam path 59, while the imaging beam path 39 is reflected from the beam splitter 51. Moreover, the beam splitter 51 is made of a plate having two optical surfaces, wherein one surface carries a semi-reflective coating to reflect the imaging beam path. The plate of the beam splitter 51 is oriented such that the reflective surface is oriented towards the object plane 37. This has an advantage that the imaging beam path is reflected from the beam splitter without traversing or entering the plate of the beam splitter 51 such that the transparent medium of the plate or refraction at the surfaces thereof do not deteriorate the imaging quality.

However, in other embodiments of the invention, it is possible to arrange the bright field illumination beam path and the imaging beam path such that the imaging beam path traverses the beam splitter while the bright field illumination beam path is reflected from the beam splitter.

The optics of the inspection system 31 further provides a dark field illumination beam path 81. The dark field illumination beam path comprises a high power broadband light source 83, which is in the present embodiment a xenon-arc lamp having an electrical power of 1500 W. The light emitted from the source 83 is collimated by one or more lenses 85 and reflected from mirrors 87 and 88 which have a function of both folding the beam path and shaping the spectrum of the dark field illumination light by allowing long wavelength components of the spectrum, such as infrared light, to traverse the mirrors 87 such that they are no longer contained in the dark field illumination light supplied to the object surface 33.

The dark field illumination beam path 81 further comprises a light manipulating optics 89 and mirrors 91 and 92 to homogenously illuminate an aperture 93. For this purpose, the optics 89 comprises lenses and optical integrators such as fly eye lenses and glass rods. The aperture 93 defines the portion of the object plane 37 which is illuminated with the dark field illumination light. For this purpose, the aperture 93 is imaged into a region close to the wafer surface 33 using a lens group 95 and a projection lens 97 wherein the beam path is again folded by mirrors 99, 101 and 103.

It is apparent from FIG. 3 that the wafer surface 33 or object plane 37 of the imaging beam path are oriented under an acute angle relative to the optical axis of the dark field illumination beam path when incident on the object plane 37. Further, the portion of the wafer surface 33 illuminated with the full intensity of dark field illumination beam should not include a periphery of the wafer since this would generate a considerable amount of stray light which might enter the image detector 43 and deteriorate a dark field image detected with the image detector. Therefore, it should be avoided that a significant intensity of the dark field illumination light is incident on the periphery of the wafer, while it is desirable that the interior surface of the wafer is homogenously illuminated. This can be achieved by optimizing a shape of the aperture 93 such that it has a non-circular curved shape. Details of such optimization are illustrated in US 2005/0146719 A1, the full disclosure of which is incorporated herein by reference.

Since the optics of the dark field illumination beam path 81 is designed such that the circular surface 33 of the wafer 35 is substantially homogenously illuminated with dark field illumination light incident on the surface under an angle $\alpha$ of about 30°, it is apparent that the dark field illumination light beam traversing the projection lens 97 has an elliptical cross section. The projection lens 97 also has a non-circular shape wherein portions which do not contribute to shaping of the dark field illumination light beam have been cut away from an originally circular lens to avoid unnecessary weight and consumption of available space.

In the present example, the projection lens 97 of the dark field illumination beam path 81 has the same optical data as the objective lens 45 of the imaging beam path 39. In particular, a surface 105 of lens 97 oriented towards the object plane 37 has a same radius of curvature as surface 55 of lens 45, and a surface 106 of lens 97 oriented towards the dark field light source 83 has a flat surface. Such usage of the same types of lenses in the dark field illumination beam path and the imaging beam path is suitable to save costs of manufacture of the inspection system.

Figure 4:
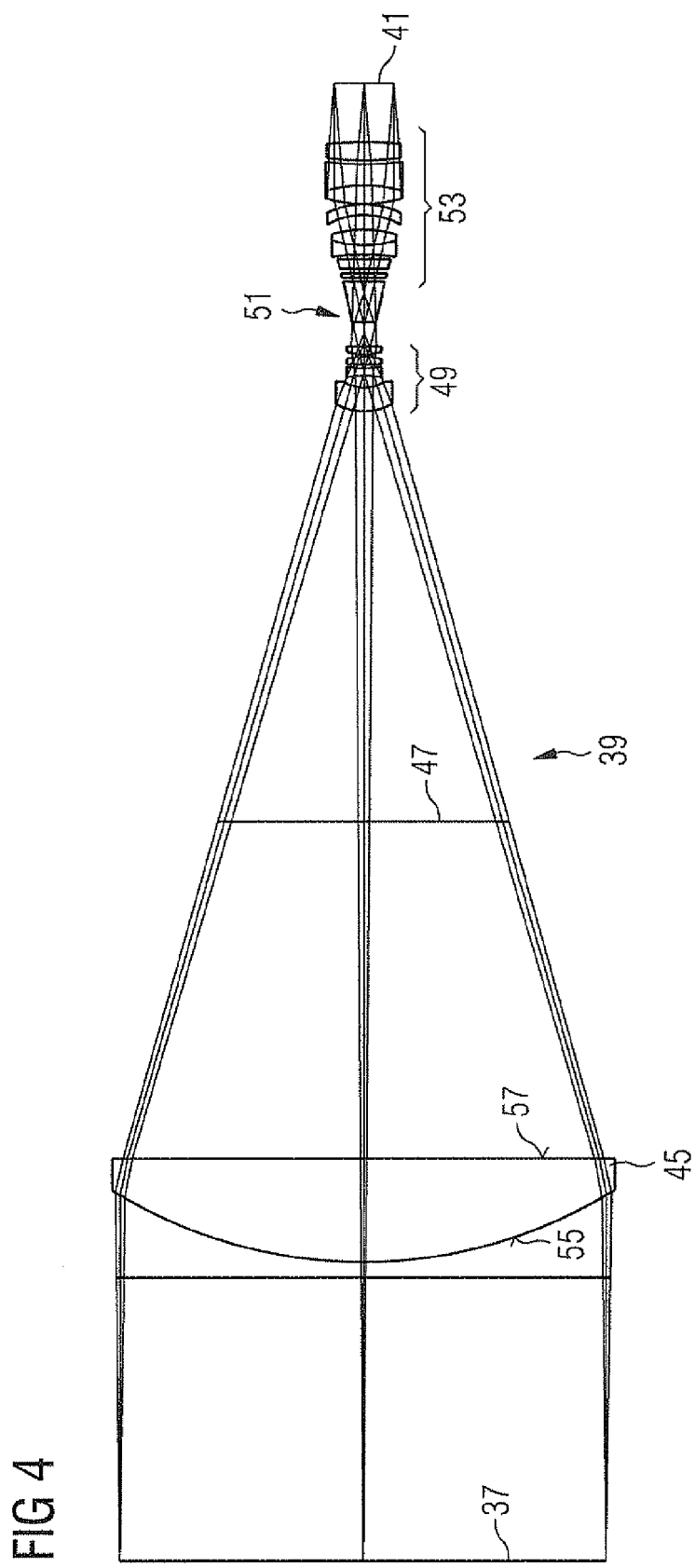
FIG. 4 is an illustration of an imaging beam path of the embodiment schematically shown in FIG. 3.

FIG. 4 is a detailed illustration of the imaging beam path 39, wherein the beam splitter 51 is not shown in FIG. 4, but the position of the beam splitter is indicated by reference numeral 51. It is apparent that the beam splitter 51 is disposed in a region of the imaging beam path 39 where a pupil plane of the imaging of the object plane 37 into the image plane 41 is formed.

Optical data of the components of the imaging beam path 39 are shown in Table 1 below, wherein the column "glass" indicates optical materials according to the nomenclature of SCHOTT and OHARA:

TABLE 1

| Surf | Type | Radius of curvature [mm] | Thickness [mm] | Glass | Free Diameter [mm] | Comment |
|---|---|---|---|---|---|---|
| OBJ | STANDARD | Infinity | 174 | | 301 | |
| 1 | STANDARD | Infinity | 10 | | 308.0416 | Additional |

TABLE 1-continued

| Surf | Type | Radius of curvature [mm] | Thickness [mm] | Glass | Free Diameter [mm] | Comment |
|---|---|---|---|---|---|---|
| 2 | COORDBRK | — | 0 | | — | Surface Element Tilt |
| 3 | STANDARD | 305.3 | 62 | N-BK7 | 310.159 | |
| 4 | STANDARD | Infinity | −62 | | 302.9163 | |
| 5 | COORDBRK | — | 62 | | — | Element Tilt |
| 6 | STANDARD | Infinity | 208.56 | | 302.9163 | Max = 465 |
| 7 | STANDARD | Infinity | 256.39 | | 182.858 | 1. Mirror |
| 8 | STANDARD | 29.322 | 14.06995 | N-SSK5 | 32.44716 | |
| 9 | STANDARD | 21.596 | 7.110291 | | 22 | |
| 10 | STANDARD | −39.383 | 5.592504 | LAFN7 | 20.21797 | |
| 11 | STANDARD | 76.351 | 2.138976 | | 19.38703 | |
| 12 | STANDARD | −73.124 | 5.813038 | N-LAK14 | 19.38848 | |
| 13 | STANDARD | −45.479 | 0.6421531 | | 20.01052 | |
| 14 | STANDARD | 63.096 | 5.149779 | N-LAK10 | 19.71157 | |
| 15 | STANDARD | −73.918 | 14.5 | | 18.95065 | 311.4 |
| STO | STANDARD | Infinity | 25 | | 14.60514 | 2. Beam Splitter |
| 17 | STANDARD | Infinity | 3 | | 26.64142 | Color Wheel |
| 18 | STANDARD | Infinity | 2.2 | BK7 | 28.14084 | Filter |
| 19 | STANDARD | Infinity | 3 | | 28.84776 | Color Wheel |
| 20 | STANDARD | Infinity | 6 | | 30.34717 | shutter |
| 21 | STANDARD | Infinity | 3 | | 33.346 | |
| 22 | STANDARD | −91.398 | 5.764071 | LLF1 | 34.04609 | |
| 23 | STANDARD | 112.61 | 10.73259 | N-PSK53 | 38.14386 | |
| 24 | STANDARD | −37.449 | 8.541288 | | 39.58976 | |
| 25 | STANDARD | −31.396 | 4.996902 | SF1 | 39.02309 | |
| 26 | STANDARD | −59.352 | 0.09566185 | | 43.5983 | |
| 27 | STANDARD | 60.213 | 12.15615 | N-SSK5 | 47.8217 | |
| 28 | STANDARD | −85.976 | 13.22124 | N-KZFS4 | 47.45478 | |
| 29 | STANDARD | 132.4 | 3.395106 | | 45.3592 | |
| 30 | STANDARD | 232.91 | 9.686887 | LAFN7 | 45.44828 | |
| 31 | STANDARD | −359.96 | 1 | | 44.92545 | |
| 32 | STANDARD | Infinity | 36.02343 | | 44.55453 | Fix 31 |
| IMA | STANDARD | Infinity | | | 36.78733 | |

The above illustrated imaging system is particularly well suited for dark field imaging. In a dark field imaging setup, a defect on the wafer which is even smaller than the imaging resolution of the imaging system generates stray light which can be detected by the image sensor. For this purpose, it is desirable to concentrate the generated stray light on a low number of pixels of the image sensor to produce detectable light intensities which are above a noise level of the pixel detectors. This means that light emanating from a point at the wafer generates an illuminated region on the image sensor which is as small as possible. Such illuminated region is referred to as a blur spot in the art. It is not possible to generate an infinitesimal small blur spot since imaging aberrations and chromatic operations contribute to enlarging the blur spot.

Table 2 below illustrates blur spot sizes at various locations in the imaging optics of the embodiment presented in table 1 above. The blur spot sizes of table 2 were calculated using the optical design software ZEMAX of Jun. 24, 2008 made by ZEMAX Development Corporation, Bellevue, Wash., USA.

TABLE 2

| Radius at object plane | Blur spot size (1) after big lens | Blur spot size (2) after first lens group | Ratio (2)/(1) | Blur spot size (3) after second lens group | Ratio (2)/(3) |
|---|---|---|---|---|---|
| 0 | 2545.24 | 7182.34 | 2.8 | 13.86 | 518.16 |
| −60 | 2846.61 | 7193.71 | 2.53 | 17.61 | 408.59 |
| −90 | 3107.50 | 7295.59 | 2.35 | 20.31 | 359.21 |
| −120 | 3593.16 | 7222.97 | 2.01 | 23.79 | 303.63 |
| −150 | 4621.14 | 7250.00 | 1.56 | 31.52 | 230.03 |

The lines of table 2 relate to light emanating from infinitesimal small points on the wafer, wherein the first column indicates a radial position in millimeters from the centre of the wafer for the respective spot. Column 2 indicates a geometrical diameter in micrometer of blur spots generated immediately after the big lens 45. Column 3 indicates blur spot diameters in micrometer generated in the beam path after the first lens group 49. Column 5 indicates blur spot diameters generated after the second lens group 53 on the detector surface. Column 4 shows ratios of the numbers given in columns 2 and 3, respectively, and column 6 shows ratios of the numbers given in column 3 and 5, respectively.

It is apparent from table 2 that the blur spot sizes increase along the beam path through the big lens 45 and the first lens group 49, and that the second lens group 53 is quite effective in reducing the blur spot sizes on the image sensor. A diameter of the pixels of the image sensor in the illustrated embodiment is 13 μm. The blur spot size is less than four times, and in particular less than three times the pixel diameter at all locations of the image sensor, accordingly.

Figure 5:
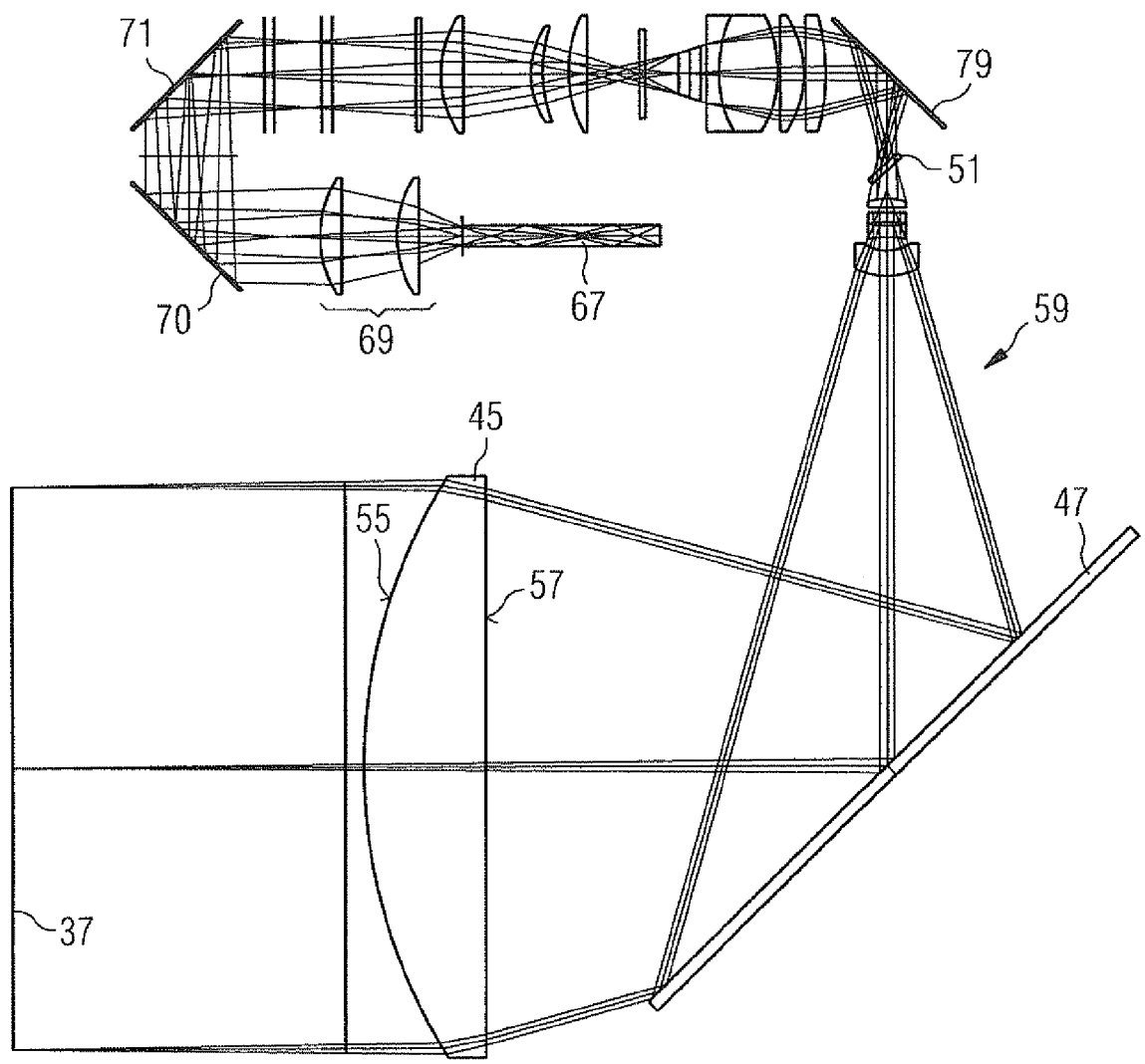
FIG. 5 is an illustration of a bright field illumination beam path of the embodiment schematically shown in FIG. 3.

FIG. 5 is a detailed illustration of the bright field illumination beam path, wherein components of the bright field illumination system upstream of the optical fiber 67 are not shown in FIG. 5.

Optical data of the components included in the bright field illumination system are shown in Table 3 below:

TABLE 3

| Surf | Type | Radius of curvature [mm] | Thickness [mm] | Glass | Free Diameter [mm] | Comment |
|---|---|---|---|---|---|---|
| OBJ | STANDARD | Infinity | 174 | | 296 | |
| 1 | STANDARD | Infinity | 10 | | 302.4957 | Additional Surface |
| 2 | COORDBRK | — | 0 | | — | Element Tilt |
| 3 | STANDARD | 305.3 | 62 | N-BK7 | 304.3861 | |
| 4 | STANDARD | Infinity | −62 | | 296.6796 | |
| 5 | COORDBRK | — | 62 | | — | Element Tilt |
| 6 | STANDARD | Infinity | 208.56 | | 296.6796 | Max = 465 |
| 7 | COORDBRK | — | 0 | | — | |
| 8 | STANDARD | Infinity | 0 | MIRROR | 352.6987 | 1. Mirror |
| 9 | COORDBRK | — | −256.39 | | — | |
| 10 | STANDARD | −29.322 | −14.06995 | N-SSK5 | 31.88391 | |
| 11 | STANDARD | −21.596 | −7.110291 | | 22 | |
| 12 | STANDARD | 39.383 | −5.592504 | LAFN7 | 19.78167 | |
| 13 | STANDARD | −76.351 | −2.138976 | | 18.96394 | |
| 14 | STANDARD | 73.124 | −5.813038 | N-LAK14 | 18.95843 | |
| 15 | STANDARD | 45.479 | −0.6421531 | | 19.52432 | |
| 16 | STANDARD | −63.096 | −5.149779 | N-LAK10 | 19.23332 | |
| 17 | STANDARD | 73.918 | −14.5 | | 18.46875 | 311.4 |
| 18 | COORDBRK | — | 0 | | — | |
| STO | STANDARD | Infinity | −3 | BK7 | 19.68119 | 1. Beam Splitter |
| 20 | STANDARD | Infinity | 0 | | 16.37627 | |
| 21 | COORDBRK | — | 0 | | — | |
| 22 | STANDARD | Infinity | −50 | | 30 | |
| 23 | COORDBRK | — | 0 | | — | |
| 24 | STANDARD | Infinity | 0 | MIRROR | 75 | |
| 25 | COORDBRK | — | 0 | | — | |
| 26 | STANDARD | Infinity | 30 | | 28.3432 | |
| 27 | STANDARD | 95.964 | 10.6 | BK7 | 60 | 01LPX263 |
| 28 | STANDARD | Infinity | 1 | | 60 | |
| 29 | STANDARD | 51.872 | 12.5 | BK7 | 60 | 01LPX183 |
| 30 | STANDARD | Infinity | 1 | | 60 | |
| 31 | STANDARD | 69.027 | 31 | N-BAF10 | 60 | 01LAO815 |
| 32 | STANDARD | −55.96 | 7 | SF11 | 60 | |
| 33 | STANDARD | −315.303 | 2 | | 60 | |
| 34 | STANDARD | Infinity | 6 | | 28.86784 | field mask if needed |
| 35 | STANDARD | Infinity | 6 | | 24.48367 | Rim mask |
| 36 | STANDARD | Infinity | 16.5 | | 21.66792 | field mask if needed |
| 37 | STANDARD | Infinity | 3 | BK7 | 46 | MIk Polfilter |
| 38 | STANDARD | Infinity | 11 | | 46 | |
| 39 | STANDARD | Infinity | 16.2 | | 8.021884 | Irisblende |
| 40 | STANDARD | Infinity | 10.6 | BK7 | 60 | |
| 41 | STANDARD | −62.247 | 12 | | 60 | 01LPX209 |
| 42 | STANDARD | −90 | 7 | BK7 | 50 | |
| 43 | STANDARD | −42.52 | 33.3 | | 50 | 33.27 |
| 44 | STANDARD | Infinity | 12.5 | BK7 | 60 | |
| 45 | STANDARD | −51.872 | 10 | | 60 | |
| 46 | STANDARD | Infinity | 2.2 | BK7 | 58 | UV Filter/ Maske |
| 47 | STANDARD | Infinity | 43.2 | | 58 | |
| 48 | STANDARD | Infinity | 5 | | 60 | array if needed |
| 49 | STANDARD | Infinity | 25 | | 60 | |
| 50 | STANDARD | Infinity | 5 | | 60 | array if needed |
| 51 | STANDARD | Infinity | 0 | | 60 | |
| 52 | STANDARD | Infinity | 40 | | 34.40161 | |
| 53 | COORDBRK | — | 0 | | — | |
| 54 | STANDARD | Infinity | 0 | MIRROR | 90 | KL mirror 74.6 × 6 |
| 55 | COORDBRK | — | 0 | | — | |
| 56 | STANDARD | Infinity | −42.25 | | 38.52066 | |
| 57 | STANDARD | Infinity | −42.25 | | 50 | |
| 58 | COORDBRK | — | 0 | | — | |
| 59 | STANDARD | Infinity | 0 | MIRROR | 75 | |
| 60 | COORDBRK | — | 0 | | — | |
| 61 | STANDARD | Infinity | 5 | | 47.42887 | |
| 62 | STANDARD | Infinity | 63.2 | | 47.95598 | |
| 63 | STANDARD | 51.872 | 12.5 | BK7 | 60 | f 156 mm |
| 64 | STANDARD | Infinity | 26 | | 60 | |
| 65 | EVENASPH | 51.872 | 12.5 | BK7 | 60 | f 100 mm |
| 66 | STANDARD | Infinity | 22 | | 60 | |
| 67 | STANDARD | Infinity | 1 | | 20 | Rod start |

TABLE 3-continued

| Surf | Type | Radius of curvature [mm] | Thickness [mm] | Glass | Free Diameter [mm] | Comment |
|---|---|---|---|---|---|---|
| 68 | NONSEQCO | Infinity | 0 | | 30 | |
| 69 | STANDARD | Infinity | 5 | | 10 | |
| IMA | STANDARD | Infinity | | 10 | | Rod end |

The bright field illumination system is configured to substantially homogenously illuminate the wafer surface 33 with bright field illumination light, wherein an outer periphery of the wafer is illuminated with a reduced light intensity. This is further illustrated with reference to FIG. 6 below.

The lower portion of FIG. 6 schematically illustrates a cross section of wafer 35, wherein the wafer 35 is a 300 mm wafer having a flat upper surface 33 and a chamfered portion 131 starting at a radius $r_2$ of about 149 mm as measured from the center of the wafer 35. The maximum radius $r_1$ of the wafer 35 and outer end of the chamfered portion 131 is at about 150.5 mm. These geometrical data of the wafer are exemplary data, wherein a geometry of wafers generally follows a standard as defined in FIG. 6 and table 3 of the document referred to as SEMI-M1-11/6.

The upper portion of FIG. 6 is a schematic illustration of a graph representing the bright field illumination light intensity I incident on the object plane 37 in dependence of the radius r. An inner portion of the wafer surface 33 up to a radius $r_3$=147 mm is used for manufacturing semiconductor circuits in this region. This region is to be illuminated with a high, substantially same light intensity. A maximum light intensity within this inner portion is indicated as $I_{max}$ in FIG. 6, and a minimum light intensity within this portion is indicated as $I_{min}$. An intensity $I_2$ at radius $r_3$ should be at least 0.900 times the maximum intensity $I_{max}$ to ensure a high image quality. Further, a light intensity $I_1$ at radius $r_1$ should be within a range of 0.001 times the maximum intensity $I_{max}$ to 0.010 times the maximum intensity $I_{max}$ to allow detection of the periphery of the wafer 35 in the image recorded by the image detector 43, while avoiding an excessive amount of stray light generated at the periphery of the wafer.

Figure 7A:
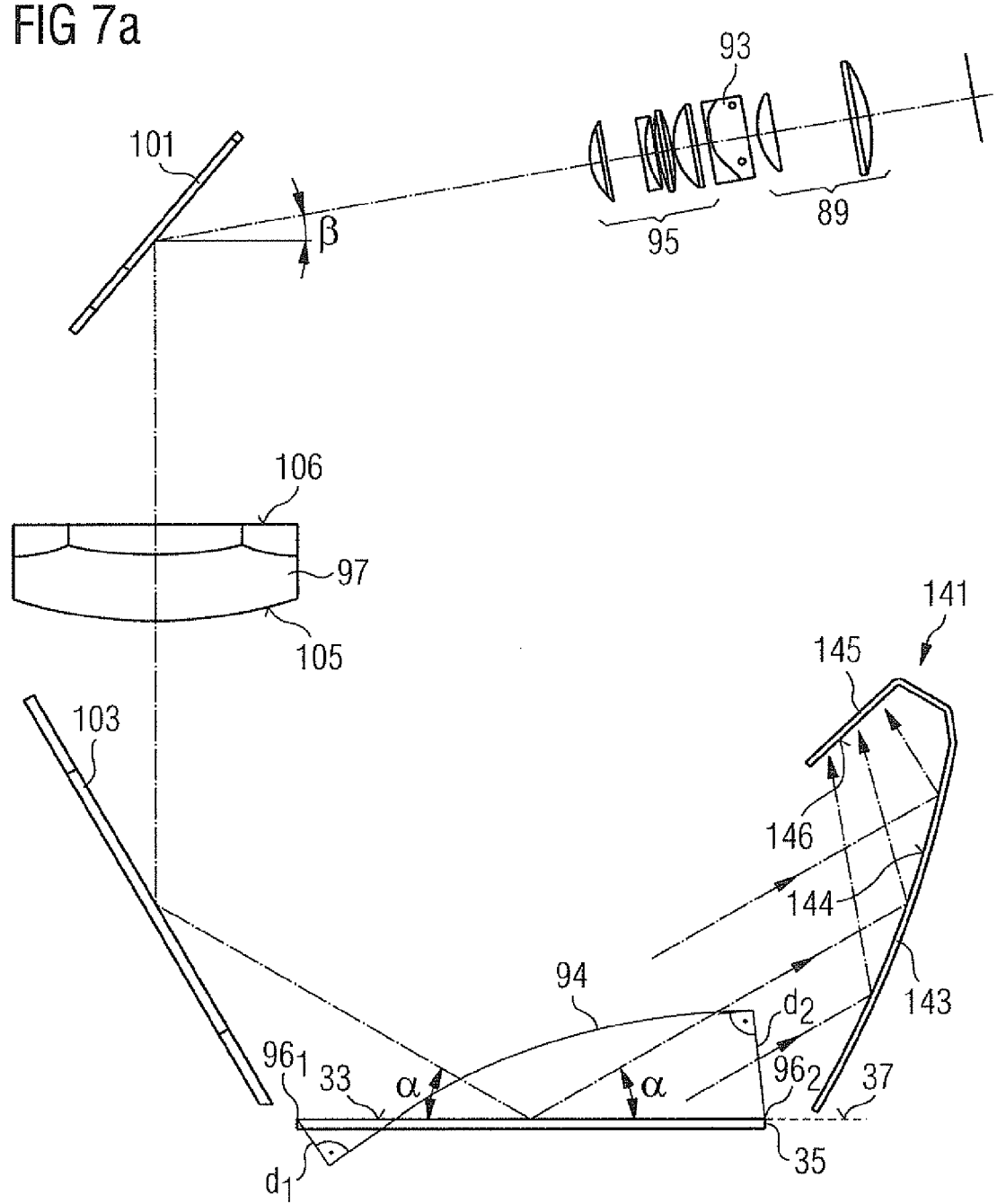
FIGS. 7a and 7b are illustrations of a dark field illumination beam path of the system schematically shown in FIG. 3.
Figure 7B:
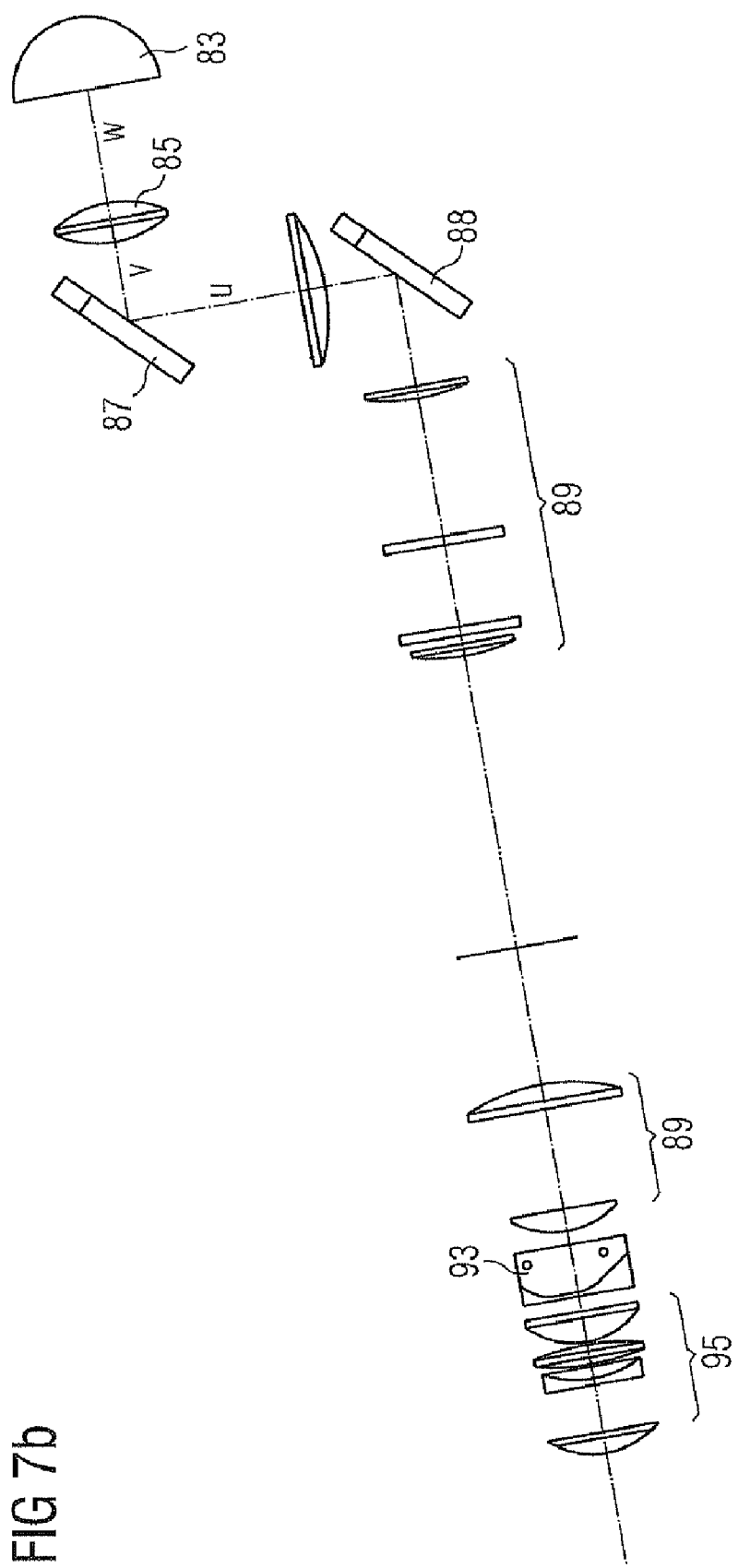

FIGS. 7a and 7b are more detailed illustrations of the dark field illumination beam path 81, wherein optical data of the components used for providing the dark field illumination beam path are shown in Table 4 below:

TABLE 4

| Surf | Type | Radius of curvature 1 [mm] | Radius of curvature 2 [mm] | Thickness | Glass |
|---|---|---|---|---|---|
| 1 | Wafer | Plano | plano | | |
| 2 | Beam dump | plano | plano | 3 | NG9-Filter |
| 3 | Mirror | plano | plano | 6 | BK7 |
| 4 | Lens | 305.3 | plano | 62 | BK7 |
| 5 | Mirror | plano | plano | 6 | BK7 |
| 6 | Lens | 41.498 | plano | 10.4 | BK7 |
| 7 | Lens | plano | −38.907 | 3 | BK7 |
| 8 | Lens | 98.171 | 98.171 | 10.7 | BK7 |
| 9 | Lens | 35.484 | −151.942 | 12.4 | BK7 |
| 10 | Mask | | | | Metal foil |
| 11 | Cylinder lens | 51.6796 | plano | 8 | BK7 |
| 12 | Lens | plano | 95.964 | 10.6 | BK7 |
| 13 | Polarizer | plano | plano | 0.7 | Quartz 1737F |
| 14 | Lens | 155.62 | plano | 4 | BK7 |
| 15 | Lens Array | plano | 32.356 | 4.5 | BK7 |
| 16 | Lens Array | 32.356 | plano | 4.5 | BK7 |
| 17 | Lens | 194.513 | plano | 4 | BK7 |
| 18 | Linosfilter | plano | plano | 10 | Quartz |
| 19 | Lens | 95.964 | plano | 10.6 | BK7 |
| 20 | Linosfilter | plano | plano | 10 | Quartz |
| 21 | Condenser | 42.738 | 42.738 | 19.733 | Quartz |
| 22 | Lamp PE1500W | | | | |

The dark field illumination beam path is a folded beam path wherein not all folding mirrors are shown in FIGS. 7a and 7b. An angle of incidence of the dark field illumination light on the wafer surface 33 and object plane 37 is α=30°. A portion of the beam path between folding mirrors 101 and 103 is oriented orthogonal to the object plane 37, and a portion of the beam path immediately upstream of folding mirror 101 is oriented under an angle β=10° relative to the object plane 37.

The dark field illumination light reflected from the wafer surface 33 is incident on a beam dump 141 which has a function to absorb the reflected illumination light. The beam dump 141 comprises a first portion 143 having a surface 144 arranged such that all dark field illumination light specularly reflected from the wafer surface 33 is incident on surface 144 of the first light absorbing portion 143 of the beam dump 141. The portion 143 is made of a dark glass, such as N9 available from SCHOTT. A transmission T of this material is within a range from 0.02 to 0.14 at a thickness of 1 mm for light within a wavelength range from 200 nm to 800 nm, and wherein T is a ratio of incident light intensity to transmitted light intensity. Surface 144 carries an anti-reflective coating. The glass has a thickness of about 5 mm, which is sufficient to substantially completely absorb that portion of the light incident on surface 144 and entering the bulk material of the portion 143. However, a small amount of light is specularly reflected from surface 144, and this amount of light is then incident on surface 146 of a second portion 145 of the beam dump 141. The second portion 145 of the beam dump is also made of an absorbing material such as dark glass and its surface 146 carries an anti-reflective coating. With such two stage arrangement of the beam dump, it is possible to provide a sufficient absorption of the dark field illumination light reflected from the wafer surface 133.

As shown in FIG. 7a, the surface 144 of the first portion 143 of the beam dump 141 is a curved surface such that surface 146 of the second portion 145 which has to receive substantially all light reflected from surface 144 can have a reduced size as compared to surface 144. This allows for a relatively small total size of the beam dump 141. In the illustrated embodiment, the curved surface 144 schematically shown in FIG. 7a is approximated by plural tiles of rectangular glass plates 148 (shown in FIG. 13) having flat surfaces.

FIG. 7a also illustrates a detail of the imaging of the aperture 93 into a region close to the wafer surface 33. In general it might not be possible to design the aperture 93 and the imaging optics 95, 97 such that the image of the aperture 93 exactly coincides with the wafer surface 33. Reference numeral 94 in FIG. 7a designates the (curved) surface on which the image of aperture 93 is generated. This surface 94 does not coincide with the wafer surface 33. However, the imaging optics is designed such that a distance between the wafer surface 33 and the image 94 of the aperture 93 is smaller at a side of the wafer which is closer to the dark field light source along the dark field illumination beam path. In particular, FIG. 7a shows a distance d1 between the image 94 of the aperture 93 and a point $96_1$ on the wafer surface 33 which is closest to the dark field light source, and a distance d2 between the image 94 of the aperture 93 and a point $96_2$ of the wafer surface which is farther away from the dark field light source.

While the illustration in FIG. 7a is exaggerated for purposes of illustration, the following relation is fulfilled in exemplary embodiments of the illustrated apparatus: d1/d2<0.8, and according to particular embodiments d1/d2 can be less than 0.5 or 0.2.

Since the image 94 of the aperture 93 and the wafer surface 33 do not coincide inside exactly, the image of the aperture 93 as projected onto the wafer surface is not a sharp image. However, the imaging quality of the aperture onto the wafer surface is better at those portions of the wafer which are closer to the dark field light source as compared to those portions which are farther away from the dark field light source. With such arrangement it is possible to achieve illumination of the wafer surface with a high intensity while avoiding illumination of the edge of the wafer which is closer to the dark field light source with dark field illumination light which would generate stray light which might than be detected and deteriorate the desired dark field image.

Figure 8:
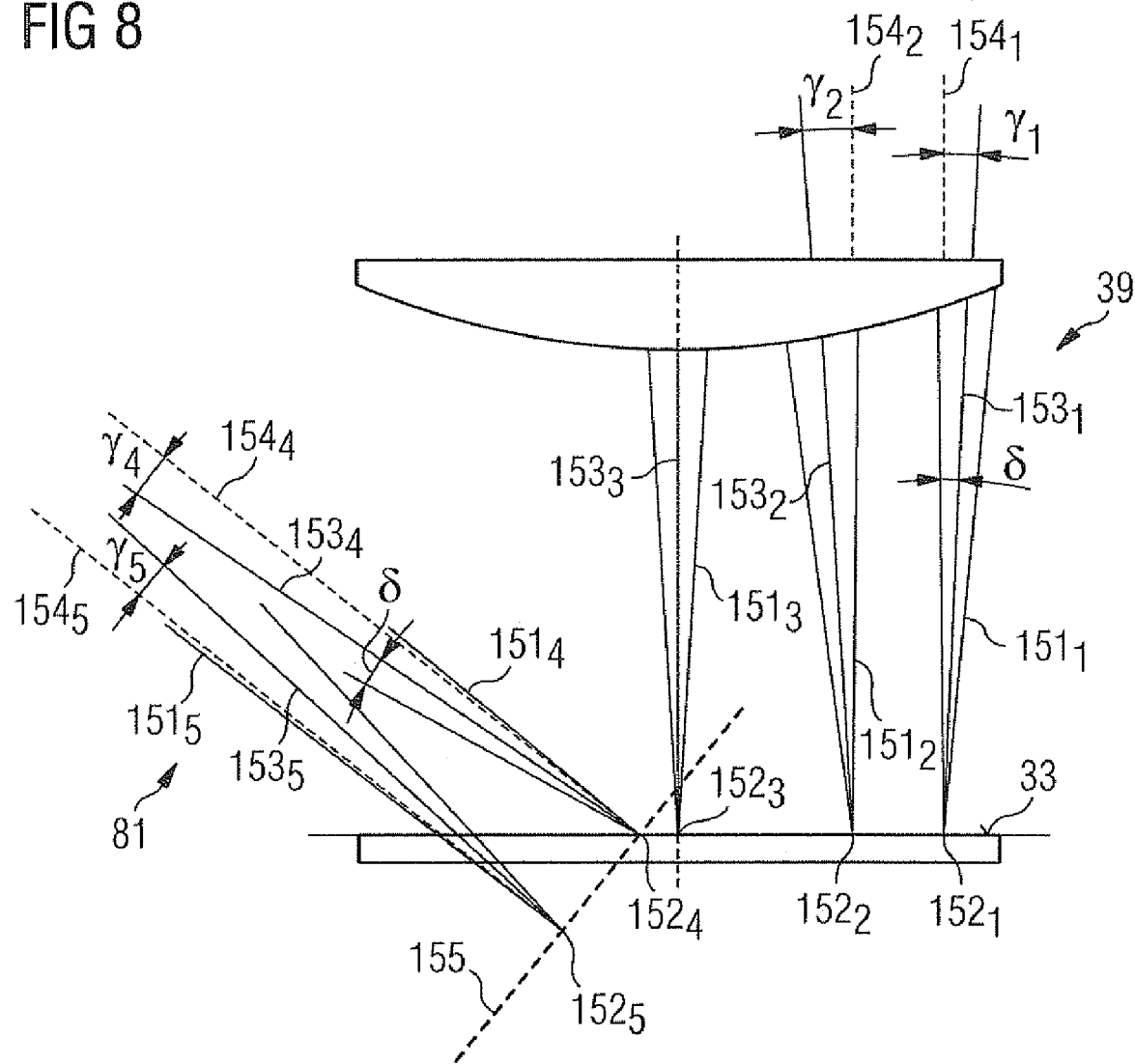
FIG. 8 is a schematic illustration of properties of the imaging beam path and the dark field illumination beam path of the system schematically shown in FIG. 3.

FIG. 8 is an illustration of geometric relations relating to numerical apertures and telecentric properties of the imaging beam path 39 and the dark field illumination beam path 81. FIG. 8 shows three light cones $151_1$, $151_2$, $151_3$ originating from three exemplary locations $152_1$, $152_2$, $152_3$ on the wafer surface 33. While light is emitted from those locations $152_1$, $152_2$, $152_3$ into substantially all directions in the half space above the wafer surface 33, only those light rays which are within the cones $151_1$, $151_2$, $151_3$ are accepted by the imaging optics and used for imaging of the wafer surface onto the radiation sensitive substrate 4 of image detector 43. The sine of the half opening angle 8 of the light cones $151_1$, $151_2$, $151_3$ is also referred to as the numerical aperture on the object side of the imaging optics. In the illustrated embodiment, the numerical aperture NA of the imaging optics has a value of about 0.015.

FIG. 8 also shows angles γ between chief rays $153_1$, $153_2$, $153_3$ of the light cones $151_1$, $151_2$, $151_3$ and surface normals $154_1$, $154_2$ of the wafer surface 33. The imaging optics of the present embodiment has a telecentric property such that a maximum value of angles γ for all light cones $151_1$, $151_2$, $151_3$ used for imaging is less than about 4°.

FIG. 8 also illustrates two cones $151_4$ and $151_5$ of rays of the dark field illumination light directed to two exemplary locations $152_4$ and $152_5$. A numerical aperture on the object side of the dark field illumination optics has a value of about 0.02 in the present embodiment. Further, chief rays $153_4$, $153_5$ of the dark field illumination light beam deviate from a common direction $154_4$, $154_5$ by angles $γ_4$, $γ_5$, respectively of less than about 4° in the present embodiment. Reference numeral 155 in FIG. 8 indicates a line orthogonal to the common direction.

The telecentric properties of both the imaging beam path 39 and the dark field illumination beam path 81 have a consequence that all locations on the wafer surface 33 receive light from substantially the same angular directions and that only light emitted into the substantially same directions is used for imaging of these locations. Angles ε between a dark field illumination light ray incident on a particular location and light rays emanating from that location and used for imaging are within a range of (90°−α)−4δ≦ε≦(90°−α)+4δ, wherein this range is determined by the numerical apertures of the imaging and dark field illumination optics. Due to the telecentric properties of the imaging optics and the dark field illumination optics, this range of angles ε is substantially the same for all locations on the wafer.

The narrow range of angles ε being the same for all portions of the wafer has an advantage in inspection of patterned wafers as will be illustrated with reference to FIGS. 9 and 10 below.

Patterned wafers carry periodic structures having characteristic dimensions which are in a region of the wavelength of the dark field illumination light and below. Such periodic structures may have an effect of a back grating on the incident light such that a significant portion of the incident light is diffracted by an angle such that it is accepted by the imaging optics.

Figure 9:
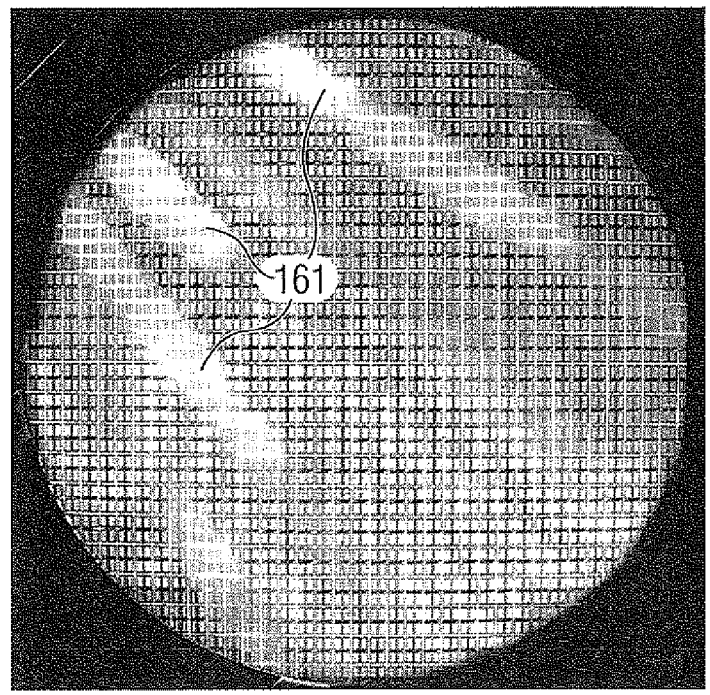
FIG. 9 is a dark field image obtainable with a conventional inspection system.

FIG. 9 is an exemplary dark field image of a patterned wafer obtained by an inspection system according to a comparative example having, as compared to embodiment of the present inventions, a low quality of its telecentric properties. FIG. 9 shows bright regions 161 in which the otherwise acceptable image of the patterned wafer is severely deteriorated. The bright regions 161 are generated by Bragg diffraction of the incident dark field illumination light at the periodic structures patterned onto the wafer. Since the inspection system used for generating the image shown in FIG. 9 has only low telecentric properties for both the imaging beam path and the dark field illumination beam path, the angular relationship between the incident light and the light used for imaging are not the same for all portions of the wafer surface. Therefore, the bright Bragg reflexes are generated only at some portions of the wafer surface where the Bragg condition is fulfilled between incident light rays and light rays used for imaging.

In this system according to the comparative example, it is possible to rotate the wafer about its center which changes the periodicity of the periodic structures on the wafer as seen by the dark field illumination light. It is thus possible to avoid generation of Bragg reflexes in the image at the positions 161 shown in FIG. 9. by rotating of the wafer. However, similar reflexes would then deteriorate the image in other regions fulfilling the Bragg condition due to the non-telecentric properties of the optics. Therefore, it is difficult to obtain a satisfactory dark field image of a patterned wafer using the dark field inspection system having a low quality of its telecentric properties.

The inspection system according to an embodiment of the present invention has relatively high quality of its telecentric properties for both the dark field illumination optics and the imaging optics such that the angular range for angles ε as illustrated above is substantially the same for all locations on the wafer. This has a consequence that, if a Bragg reflex caused by periodic structures on the wafer is generated, it will be equally generated at substantially all locations of the wafer, such that the complete image of the wafer is deteriorated by such reflexes. It is then, however, possible to rotate the wafer about its central axis by a sufficient angle such that visible Bragg reflexes are suppressed in the full image of the wafer. Using the system according to this embodiment of the invention, it is possible to obtain dark field images of patterned wafers which are substantially free of deteriorations due to Bragg reflexes.

Figure 10:
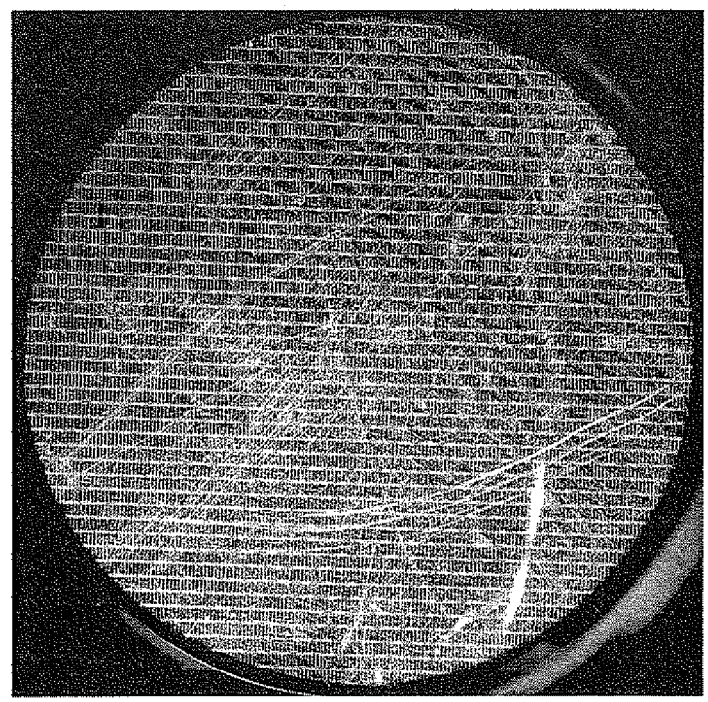
FIG. 10 is a dark field image obtained with an inspection system according to an embodiment of the invention.

FIG. 10 shows an exemplary dark field image of a patterned wafer obtainable by the inspection system according to this embodiment of the invention. This image is free of artificial reflexes generated by Bragg diffraction, and the visible structures are caused by the patterning of the wafers and defects such as scratches on the wafer.

FIGS. 4, 5 and 7 are separate illustrations of the imaging beam path 39, bright field illumination beam path 59 and dark field illumination beam path 81. These three separate beam paths are integrated to form the inspection system 31 using mounting structures including frames for the optical components, and the beam paths are folded such that the components of the inspection system can be accommodated in a rectangular housing having dimensions of 505 mm×700 mm×900 mm (height).

Figure 11:
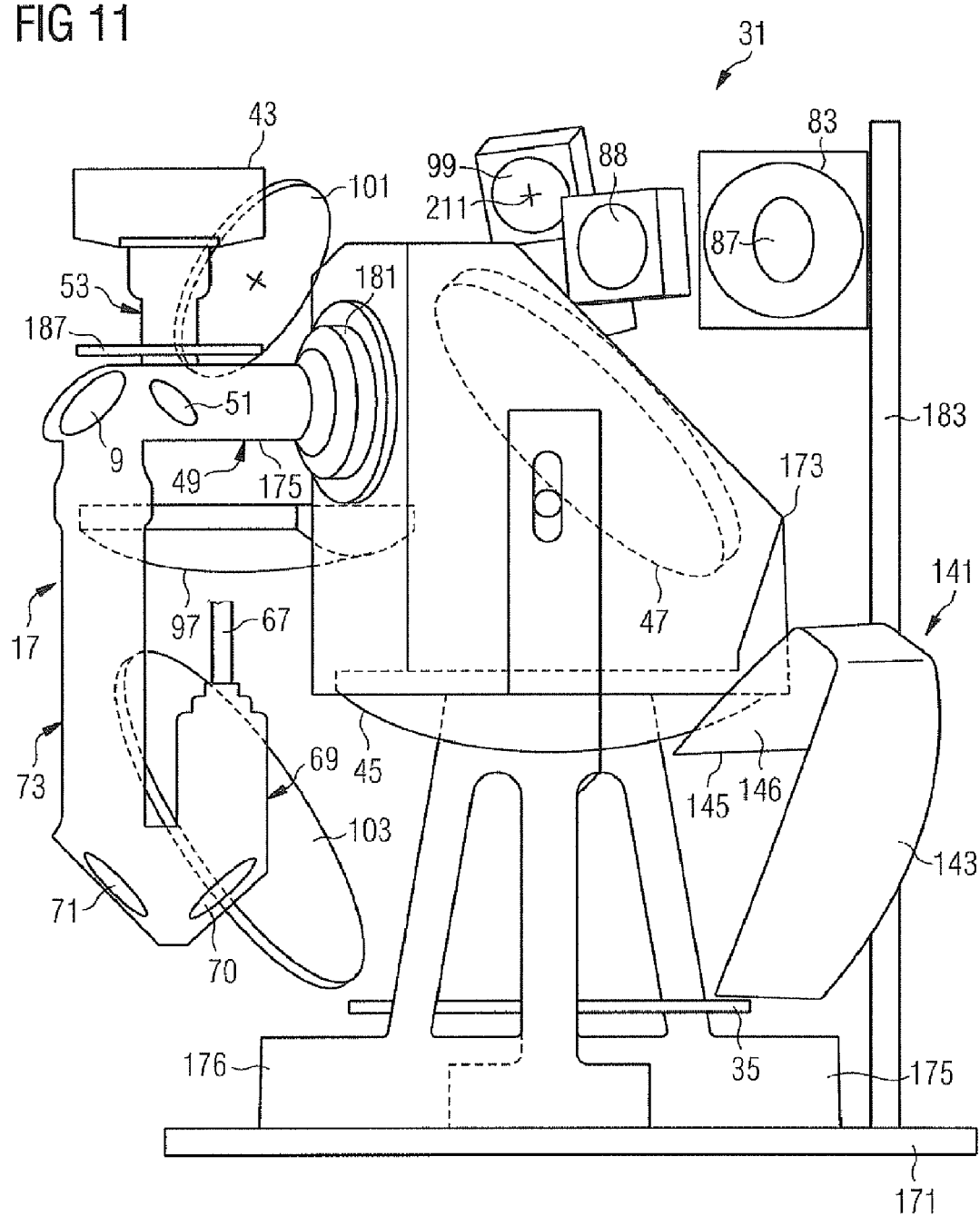
FIG. 11 is a schematic side view of the system schematically shown in FIG. 3.
Figure 12:
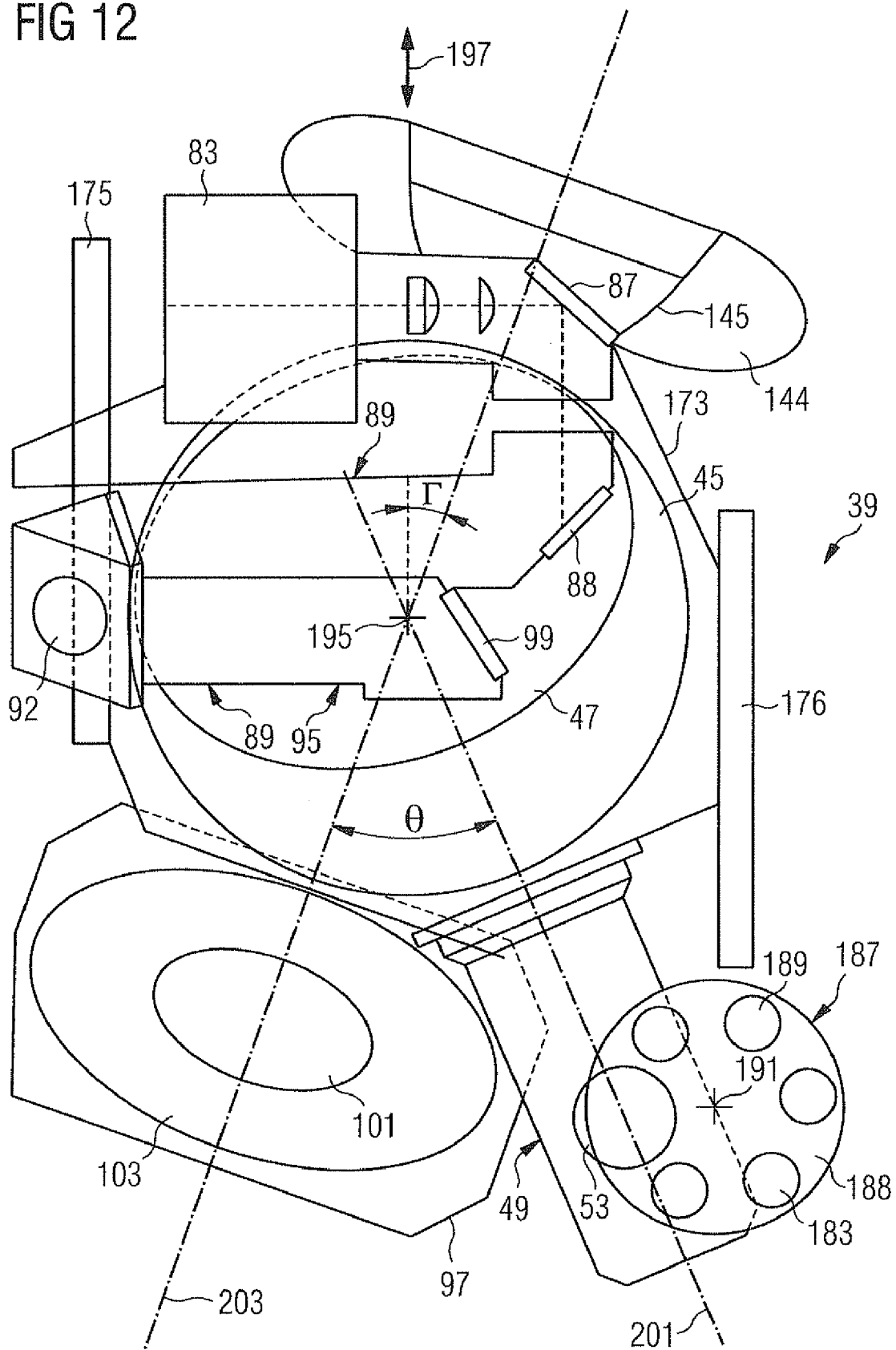
FIG. 12 is a schematic elevation view of the system schematically shown in FIG. 3.
Figure 13:
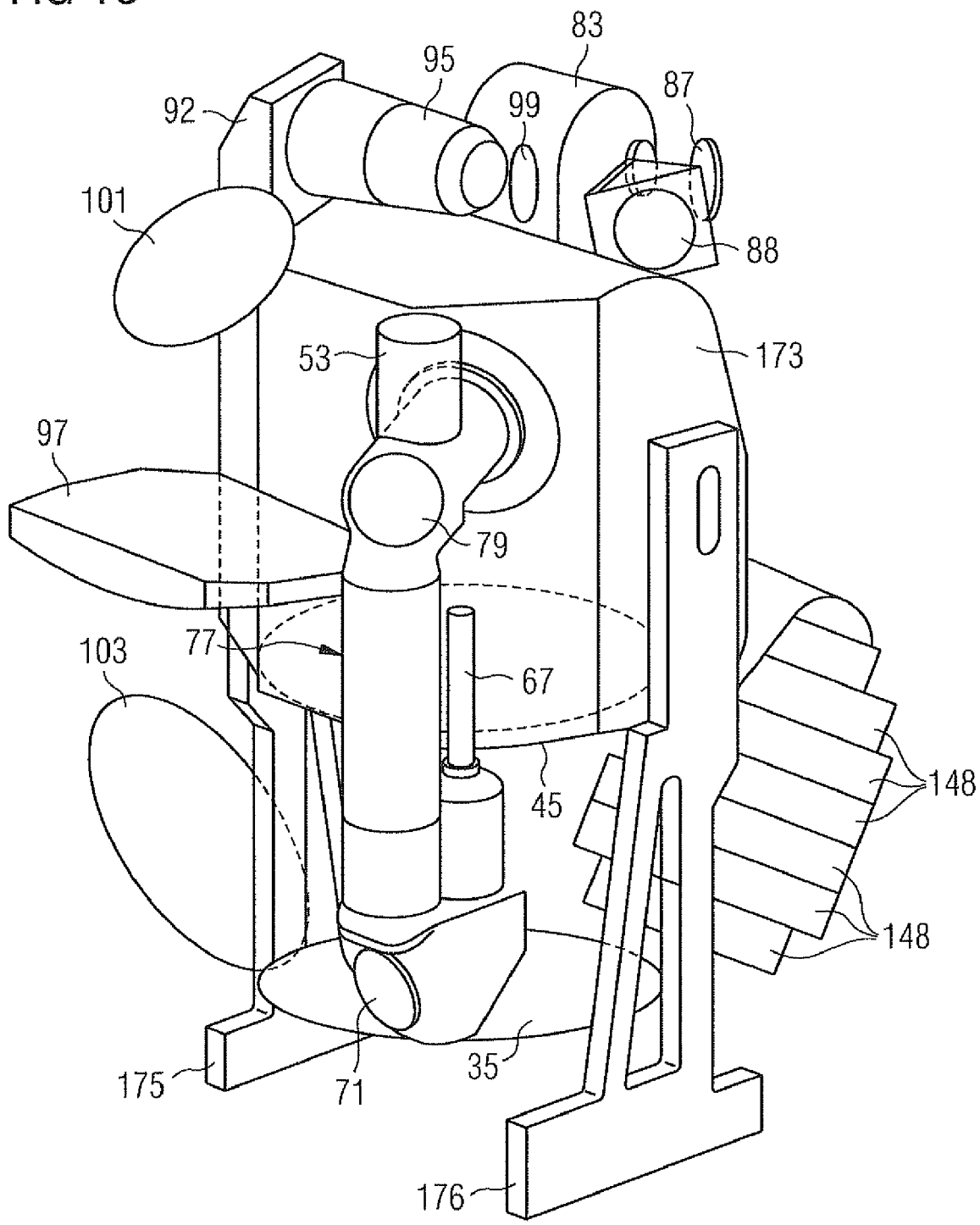
FIG. 13 is a schematic perspective view of the system schematically shown in FIG. 3.

FIGS. 11, 12 and 13 are schematic drawings for illustrating the three-dimensional arrangement of mounting structures for the optical components and the beam paths. FIGS. 11, 12 and 13 are simplified illustrations of the inspection system 31 wherein some components and mounting structures not necessary for acquiring an understanding of the three-dimensional arrangement are omitted in one or the other of FIGS. 11 to 13.

The optical components of the optical inspection system 31 are all mounted on and finally carried by a common base 171 which can be a suitable plate or socket. The most heavy components of the optical system are the objective lens 45 and folding mirror 47, which are both mounted to frames mounted on a common integral mounting structure 173 formed as a cast aluminum body. The mounting structure 173 of the objective lens 45 and mirror 47 is supported by left and right pillars 175, 176 which are supported on the base 171 such that the pillars 175, 176 carry the weight of the objective lens 145, mirror 47 and other optical and structural components mounted to the mounting structure 173.

The beam splitter 51 and lens group 49 are accommodated in a mounting tube 179 mounted to the mounting structure 173 via suitable flanges 181 such that the mounting structure 173 mounts and carries the weight of the beam splitter 51 and lens group 49. Further, components of the bright field illumination system, such as mirror 79, lens groups 77, 73 and 69 and mirrors 70, 71 are connected to tube 179 and finally supported and carried by the mounting structure 173.

The dark field illumination light source 83 is mounted to and carried by a pillar 183 which is directly supported on the base 171 such that the mounting structure 183 of the bright field light source has substantially no direct mechanical connection with the frame structure 173 apart from the fact that both rest on the common base 171.

FIG. 12 shows a color wheel 187 comprising a disc 188 having plural openings 189 in which various filters can be mounted such that one of the filters can be inserted in the imaging beam path 39 at a position between the lens group 53 and the radiation sensitive surface 41 of image detector 43 by rotating the disc 188 about an axis 191.

Reference is now made to FIG. 12 which schematically shows components of the inspection system 31 when seen from above, or, in other words, in a projection onto a plane which is parallel to the object plane 37. A center of the object field is indicated at 195. When a wafer is mounted on the object mount in its inspection position, a center of the wafer coincides with the center 195 of the object plane. A periphery of the objective lens 45 is represented in FIG. 12 by a circular line 45, and the wafer, which is not shown in FIG. 12, has a diameter which is somewhat smaller than the diameter of the lens 45. A wafer supply apparatus (not shown in FIG. 12) is configured to translate the wafer in a direction indicated by an arrow 197 to move the wafer along a path between pillars 175, 176 such that the wafer can be removed from and inserted into the system 39.

An axis 201 shown in FIG. 12 coincides with a portion of the optical axis of the imaging beam path 39 and the bright field illumination beam path 59 between folding mirror 47 and beam splitter 51 when projected onto the plane parallel to the object plane 37.

An axis 203 shown in FIG. 12 coincides with a portion of the dark field illumination beam path between folding mirror 103 and beam dump 141 when projected onto the plane parallel to the object plane 37. In the illustrated embodiment, an angle Θ between axes 201 and 203 is about 47° and an angle Γ between a direction 197 and axis 203 is 23°, which is smaller than an angle between direction 197 and axis 201.

Reference is now made to FIG. 11 which is an elevation view of components of the system 31 when seen from the side. It is apparent from FIG. 11 that a center 211 of mirror 99 in the dark field illumination beam path 81 is located substantially higher than a center 213 of mirror 101 such that a portion of the optical axis of the dark field illumination beam path between mirrors 99 and 101 is oriented under an angle β (see FIG. 7a), which is 10° in the present embodiment, relative to the object plane 37.

With the arrangement as illustrated with reference to FIGS. 11 to 13 above, it is possible to accommodate the components of the inspection system 31 within a relatively small volume and to mount the optical components such that an image quality of the system is not heavily deteriorated by vibrations induced into the system from a cooling system of the bright field light source or the dark field light source or induced into the system from outside through the base 71.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. An inspection system comprising: imaging optics for imaging an object plane into an image plane and comprising an objective lens having positive optical power, a first lens group having negative optical power and a second lens group having positive optical power arranged in this order along a common optical axis; wherein a pupil plane of the imaging optics is located between the first lens group and the second lens group; wherein the imaging optics are configured such that a first length is measured along the optical axis from a lens surface of the objective lens closest to the image plane to a lens surface of the first lens group located closest to the object plane, and at least one of the following relations is fulfilled:

i) wherein the first length measured along the optical axis from a lens surface of the objective lens closest to the image plane to a lens surface of the first lens group located closest to the object plane is greater than a second length that is a distance measured along the optical axis from the lens surface of the first lens group located closest to the object plane to a lens surface of the second lens group located closest to the image plane;

ii) wherein the first length is greater than a diameter of an object field imaged into the image plane; and iii) wherein the first length is greater than a third length that is a distance measured along the optical axis from the object plane to a lens surface of the objective lens closest to the object plane.

2. The inspection system according to claim 1 wherein a diameter of an object field imaged to the image plane is greater than 200 mm, and wherein a total extension of an imaging beam path from the object plane to the image plane is less than 1100 mm.

3. The inspection system according to claim 1 wherein a total extension of an imaging beam path from the object plane to an image plane divided by a diameter of an object field is less than 6.0.

4. The inspection system according to claim 1 wherein the first length is greater than 1.4 times the diameter of the object field imaged into the image plane.

5. The inspection system according to claim 1 wherein no additional optics having optical power are located along the optical axis between the first lens group and the second lens group.

6. The inspection system according to claim 1 wherein no additional optics having optical power are located along the optical axis between the objective lens and the first lens group.

7. The inspection system according to claim 1 wherein the first length is greater than 3 times the second length.

8. The inspection system according to claim 1 wherein the first length is greater than 2.0 times the third length.

9. The inspection system according to claim 1 wherein the objective lens is a single non-cemented lens element having a first surface and a second surface, wherein a surface curvature of the first surface is larger than a surface curvature of the second surface, and a free diameter of the objective lens divided by a radius of curvature of the first surface is greater than 0.5.

10. The inspection system according to claim 1 further comprising a beam splitter located in an imaging beam path between the first lens group and the second lens group, and a bright-field light source generating bright-field illumination light directed towards the object plane, wherein the beam splitter is located in a bright-field illumination beam path extending between the bright-field light source and the object plane.

11. The inspection system according to claim 7 wherein the first length is greater than 5 times the second length.

12. The inspection system according to claim 8 wherein the first length is greater than 2.5 times the third length.

13. The inspection system according to claim 9 wherein a lens surface of the objective lens closest to the object plane is a convex surface having a radius of curvature less than 2 m.

14. The inspection system according to claim 9 wherein a lens surface of the objective lens closest to the image plane is a substantially flat surface having a radius of curvature greater than 10 m.

15. The inspection system according to claim 10 wherein the beam splitter comprises a transparent substrate having a reflective coating on one surface thereof and is arranged such that the bright field illumination beam path traverses the substrate and the imaging beam path is reflective from the reflective coating without traversing the substrate.

16. The inspection system according to claim 10 wherein the beam splitter is located in a region of the pupil plane.

17. The inspection system according to claim 10 wherein the beam splitter is intersected by a pupil plane of the imaging beam path.

* * * * *